United States Patent

Wingert et al.

Patent Number: 5,449,809
Date of Patent: Sep. 12, 1995

[54] ACETYLENE DERIVATIVES AND CROP PROTECTION AGENTS CONTAINING THEM

[75] Inventors: Horst Wingert, Mannheim; Beate Hellendahl, Shifferstadt; Reinhard Kirstgen, Neustadt; Hubert Sauter, Mannheim; Eberhard Ammermann, Heppenheim; Gisela Lorenz, Neustadt, all of Germany

[73] Assignee: BASF Aktiengesellschaft, Ludwigshafen, Germany

[21] Appl. No.: 99,693

[22] Filed: Jul. 30, 1993

[30] Foreign Application Priority Data

Aug. 11, 1992 [DE] Germany .......... 42 26 557.6
Nov. 27, 1992 [DE] Germany .......... 42 39 874.6

[51] Int. Cl.$^6$ ............... C07C 279/00; C07C 205/00
[52] U.S. Cl. ....................... 558/412; 560/19; 560/20; 560/21; 560/22; 560/23; 560/35; 562/434; 562/435; 562/437; 562/438; 562/440
[58] Field of Search ............... 558/412, 414; 514/522; 560/19, 20, 21, 22, 23, 35; 562/434, 435, 437, 438, 440

[56] References Cited

U.S. PATENT DOCUMENTS 4,829,085 5/1989 Wender et al. .......... 564/522
4,937,372 6/1990 Wenderoth et al.

FOREIGN PATENT DOCUMENTS 0244077 11/1987 European Pat. Off.
0260794 3/1988 European Pat. Off.
2172595 9/1986 United Kingdom.

OTHER PUBLICATIONS

CA(105):78670 Bushell et al, "Fungicidal phenylacrylic acid derivative" EP 178826 AZ, 1986. Abstract only.

Primary Examiner—Raymond Henley, III
Assistant Examiner—Keith MacMillan
Attorney, Agent, or Firm—Oblon, Spivak, McClelland, Maier & Neustadt

[57] ABSTRACT

Acetylene derivatives of the general formula I

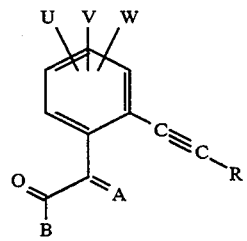

where
U, V and W are hydrogen, halogen, nitro, cyano, alkyl or alkoxy,
A is alkylidene, alkoxymethylidene, alkylthiomethylidene or alkoximino,
B is OH, alkoxy or alkylamino and
R is hydrogen, halogen, cyano, $CF_3$, alkyl, cycloalkyl, haloalkyl, aryl, alkenyl, alkynyl, heterocyclyl, hetaryl, arylalkyl, arylalkenyl, arylethynyl, hetaryl-$C_1$-$C_4$-alkyl, $C_1$-$C_4$-alkoxy-$C_1$-$C_4$-alkyl, aryloxyalkyl, hetaryloxyalkyl, arylamino-alkyl, arylthiomethyl, hetarylthiomethyl, $C(O)R^1$, $C(O)NR^2R^3$, $C(S)NR^4R^5$, $C(O)SR^6$, $C(S)OR^7$, $C(S)SR^8$, $CH(OH)R^9$, $CH(OR^{10})R^{11}$, $SiR^{12}R^{13}R^{14}$, $SnR^{15}R^{16}R^{17}$, $C(OR)R^{18}$ or $C(=N-OR^{19})R^{20}$ and
$R^1$-$R^{17}$, $R^{19}$ and $R^{20}$ are hydrogen, alkyl, aryl, hetaryl, arylalkyl or hetarylalkyl and $R^{18}$ is OH, $C_1$-$C_4$-alkoxy or aryl-$C_1$-$C_4$-alkoxy, and fungicides containing these compounds.

10 Claims, No Drawings

ACETYLENE DERIVATIVES AND CROP PROTECTION AGENTS CONTAINING THEM

The present invention relates to novel acetylene derivatives and a method for controlling pests, in particular fungi, insects, nematodes and spider mites, with these compounds.

It is known that individual acetylene derivatives (European Patents 178,826, 244,077, 253,213, 280,185 and 477,631) have fungicidal or insecticidal activity. However, their activity is unsatisfactory.

We have found, surprisingly, that the novel acetylene derivatives of the general formula I

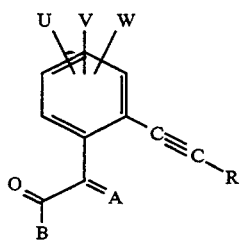

where

U, V and W are identical or different and are each hydrogen, halogen, nitro, cyano, $C_1$–$C_4$-alkyl or $C_1$–$C_4$-alkoxy, A is $C_1$–$C_4$-alkylidene, $C_1$–$C_4$-alkoxymethylidene, $C_1$–$C_4$-alkylthiomethylidene or $C_1$–$C_4$-alkoximino, B is OH, $C_1$–$C_4$-alkoxy or $C_1$–$C_4$-alkylamino, and R is hydrogen, halogen, cyano, $CF_3$, straight-chain or branched $C_1$–$C_{10}$-alkyl, $C_3$–$C_6$-cycloalkyl, unsubstituted or substituted aryl, halo-$C_1$–$C_4$-alkyl, $C_2$–$C_6$-alkenyl, $C_2$–$C_4$-alkynyl, unsubstituted or substituted heterocyclyl, unsubstituted or substituted hetaryl, unsubstituted or substituted aryl-$C_1$–$C_4$-alkyl, unsubstituted or substituted aryl-$C_2$–$C_4$-alkenyl, unsubstituted or substituted arylethynyl, unsubstituted or substituted hetaryl-$C_1$–$C_4$-alkyl, $C_1$–$C_4$-alkoxy-$C_1$–$C_4$-alkyl, unsubstituted or substituted aryloxy-$C_1$–$C_4$-alkyl, unsubstituted or substituted hetaryloxy-$C_1$–$C_4$-alkyl, unsubstituted or substituted arylamino-$C_1$–$C_4$-alkyl, unsubstituted or substituted arylthiomethyl, unsubstituted or substituted hetarylthiomethyl, $C(O)R^1$, $C(O)NR^2R^3$, $C(S)NR^4R^5$, $C(O)SR^6$, $C(S)OR^7$, $C(S)SR^8$, $CH(OH)R^9$, $CH(OR^{10})R^{11}$, $SiR^{12}R^{13}R^{14}$, $SnR^{15}R^{16}R^{17}$, $C(O)R^{18}$ or $C(=N-OR^{19})R^{20}$ and $R^1$–$R^{17}$, $R^{19}$ and $R^{20}$ are identical or different and are each hydrogen, $C_1$–$C_4$-alkyl, unsubstituted or substituted aryl, unsubstituted or substituted hetaryl, unsubstituted or substituted arylalkyl or unsubstituted or substituted hetarylalkyl, $R^{18}$ is OH, $C_1$–$C_4$-alkoxy or unsubstituted or substituted aryl-$C_1$–$C_4$-alkoxy, the term "unsubstituted or substituted" denoting, in addition to hydrogen, the substitutents halogen, cyano, nitro, $C_1$–$C_4$-alkyl, $C_1$–$C_4$-alkoxy, $C_1$–$C_4$-haloalkyl, $C_1$–$C_4$-haloalkoxy, $C_1$–$C_4$-alkoximino-$C_1$–$C_4$-alkyl, aryl, aryloxy, benzyl, benzyloxy, hetaryl, hetaryloxy, $C_3$–$C_6$-cycloalkyl, $C_1$–$C_4$-dialkylamino, $CO_2Me$, $CO_2Et$, formyl and acyl, Me being methyl, Et being ethyl and the expression hetaryl being an aromatic five-membered or sixmembered heterocyclic structure, with the exception of the following individual compounds of the general formula I where A is $CHOCH_3$, B is $OCH_3$ and R is phenyl, A is $CHSCH_3$, B is $OCH_3$ and R is phenyl, A is $CHCH_3$, B is $OCH_3$ and R is phenyl, 2-fluorophenyl, 2-chlorophenyl, 2-bromophenyl, 2-methoxyphenyl, 2-nitrophenyl, 2-methylphenyl, 4-bromophenyl, 4-trifluoromethylphenyl or 4-methylphenyl, A is $NOCH_3$, B is $OCH_3$ and R is phenyl, 2-fluorophenyl, 2-chlorophenyl, 2-bromophenyl, 2-methoxyphenyl, 2-nitrophenyl, 2-methylphenyl, 4-bromophenyl, 4-trifluoromethylphenyl or 4-methylphenyl, A is $NOCH_3$, B is $NHCH_3$ or R is $CH_3$ or phenyl, A is $CHOCH_3$, B is $NHCH_3$ and R is $CH_3$ or phenyl and A is $CHSCH_3$, B is $NHCH_3$ and R is phenyl, have excellent fungicidal, insecticidal, nematicidal and acaricidal activity.

The fungicidal and insecticidal activity is preferred.

The radicals stated for the general formula I may have, for example, the following meanings:

U, V and W may each be hydrogen, halogen (e.g. fluorine, chlorine, bromine or iodine), methyl or methoxy, A may be $C_1$–$C_4$-alkylidene (e.g. methylidene, ethylidene, n-propylidene, isopropylidene, n-butylidene, isobutylidene, sec-butylidene or tert-butylidene), $C_1$–$C_4$-alkoxymethylidene t(e.g. methoxy-, ethoxy-, n-propoxy-, iso-propoxy-, n-butoxy-, isobutoxy-, sec-butoxy- or tert-butoxymethylidene), $C_1$–$C_4$-alkylthiomethylidene (e.g. methyl-, ethyl-, n-propyl-, isopropyl-, n-butyl-, iso-butyl-, sec-butyl- or tert-butylthiomethylidene), $C_1$–$C_4$-alkoximino (e.g. methoximino, ethoximino, n-propoximino, isopropoximino, n-butoximino, isobutoximino, sec-butoximino or tert-butoximino), B may be OH, $C_1$–$C_4$-alkoxy (e.g. methoxy, ethoxy, n-propoxy, isopropoxy, n-butoxy, isobutoxy, sec-butoxy or tert-butoxy) or $C_1$–$C_4$-alkylamine (e.g. methylamine, ethylamine, n-propylamine, isopropylamine, n-butylamine, isobutylamine, sec-butylamine or tert-butylamine), and R is hydrogen, halogen (fluorine, chlorine, bromine or iodine), cyano, $CF_3$ straight-chain or branched $C_1$–$C_{10}$-alkyl (e.g. methyl, ethyl, n-propyl, isopropyl, n-butyl, isobutyl, sec-butyl, tert-butyl, n-pentyl, isopentyl, sec-pentyl, tert-pentyl, neopentyl, n-hexyl or n-decyl), $C_3$–$C_6$-cycloalkyl (e.g. cyclopropyl, cyclobutyl, cyclopentyl or cyclohexyl), unsubstituted or substituted aryl (e.g. phenyl, naphthyl or anthryl), halo-$C_1$–$C_4$-alkyl (e.g. bromomethyl, chloromethyl, iodomethyl or $CF_3$-methyl), $C_2$–$C_6$-alkenyl (e.g. vinyl, 1-propenyl, 2-propenyl, 2-butenyl, 3-butenyl, 1-methyl-2-propenyl, 3-methyl-2-butenyl or 2-methyl-2-penten-5-yl), $C_2$–$C_4$-alkynyl (e.g. ethynyl or 1-propynyl), unsubstituted or substituted heterocyclyl (e.g. oxiranyl, 1-aziridinyl, 1-azetidinyl, 1-pyrrolidinyl, 2-tetrahydrofuryl, 2-tetrahydropyranyl, 3-tetrahydropyranyl, 1-piperidinyl, 1-morpholinyl, 1-piperazinyl, 1,3-dioxanyl, 3-tetrahydrothiopyranyl), unsubstituted or substituted hetaryl (e.g. pyridyl, 2-pyridyl, 3-pyridyl, 4-pyridyl, pyrimidinyl, 4-pyrimidinyl, 2-pyrimidinyl, thienyl, 2-thienyl, 3-thienyl, furyl, 2-furyl, 3-furyl, 1-pyrrolyl, 5-isoxazolyl, 3-isoxazolyl, 1,3,4-oxadiazol-2-yl, 1,2,4-oxadiazol-5-yl, 1,3,4-thiadiazol-2-yl, 1-imidazolyl, 1,2,4-triazolyl, 1,3,4-triazolyl, 4-thiazolyl, 2-benzothiazolyl), unsubstituted or substituted aryl-$C_2$-$C_4$-alkyl (e.g. benzyl, 1-phenethyl, 2-phenethyl, 1-phenylpropyl, 2-phenylpropyl, 3-phenylpropyl, 2-methyl-3-phenylpropyl, 2-methyl-2-phenylpropyl or 4-phenylbutyl), unsubstituted or substituted aryl-$C_1$-$C_4$-alkenyl (e.g. phenyl-1-ethenyl, 2-phenyl-1-propenyl, 2,2-diphenylethenyl, 1-phenyl-1-propen-2-yl or 1-phenyl-1-ethenyl), unsubstituted or substituted arylethynyl (e.g. phenylethynyl), unsubstituted or substituted hetaryl-$C_1$-$C_4$-alkyl (e.g. pyridylmethyl or 3-pyridylmethyl), $C_1$-$C_4$-alkoxy-$C_1$-$C_4$-alkyl (e.g. methoxymethyl, ethoxymethyl, n-propoxymethyl, isopropoxymethyl, n-butoxymethyl, isobutoxymethyl, sec-butoxymethyl, tert-butoxymethyl, 2-methoxyprop-2-yl, 2-ethoxyprop-2-yl, 2-n-propoxyprop-2-yl, isopropoxyprop-2-yl, 2-n-butoxyprop-2-yl, isobutoxyprop-2-yl, sec-butoxyprop-2-yl or tert-butoxyprop-2-yl), unsubstituted or substituted aryloxy-$C_1$-$C_4$-alkyl (e.g. phenoxymethyl), unsubstituted or substituted hetaryloxy-$C_1$-$C_4$-alkyl (e.g. 2-thienyloxymethyl), unsubstituted or substituted arylamino-$C_1$-$C_4$-alkyl (e.g. N-(phenylamino)-methyl), C(O)$R^1$ (e.g. C(O)CH$_3$, C(O)CH$_2$CH$_3$ or C(O)phenyl), C(O)NR$^2$R$^3$ (e.g. C(O)NH$_2$, C(O)NHCH$_3$), C(S)NR$^2$R$^3$ (e.g. C(S)NH$_2$ or C(S)NHCH$_3$), C(O)SR$^6$ (e.g. C(O)SCH$_3$ or C(O)SCH$_2$C$_6$H$_5$), C(O)OR$^7$ (e.g. CO$_2$CH$_3$ or CO$_2$CH$_2$C$_6$H$_5$), C(S)SR$^8$ (e.g. CS$_2$CH$_3$), CH(OH)R$^9$ (e.g. H(OH)C$_6$H$_5$), CH(OR$^{10}$)R$^{11}$ (e.g. CH(OCH$_3$)C$_6$H$_5$), SiR$^{12}$R$^{13}$R$^{14}$ (e.g. SiMe$_3$) SnR$^{15}$R$^{16}$R$^{17}$ (e.g. SnMe$_3$), C(O)R$^{18}$ (e.g. CO$_2$Me, CO$_2$CH$_2$C$_6$H$_5$) or C(=N—OR$^{19}$)R$^{20}$ (e.g. C(NO-Me)C$_6$H$_5$).

$R^1$-$R^{17}$, $R^{19}$ and $R^{20}$ are, for example, hydrogen $C_1$-$C_4$-alkyl (e.g. methyl, ethyl, n- and isopropyl, n-, iso-, sec- and tert-butyl), unsubstituted or substituted aryl (e.g. 2-chlorophenyl, 3,5-dimethylphenyl and 1-methyl-2-naphthyl), unsubstituted or substituted hetaryl (e.g. 6-chloro-2-pyrridyl, 4-pyrimidinyl, 2-furyl and 6-methyl-benzthiazol-2-yl), unsubstituted or substituted arylalkyl (e.g. 2-chlorobenzyl and 3,5-dichlorobenzyl) and unsubstituted or substituted hetarylalkyl (e.g. 2-furylmethyl and 6-methyl-2-pyridylmethyl) and $R^{18}$ is, for example, OH, $C_1$-$C_4$-alkoxy (e.g. methoxy and ethoxy) and unsubstituted or substituted aryl-$C_1$-$C_4$-alkoxy (e.g. 2-chlorobenzyloxy).

The radicals defined above as unsubstituted or substituted contain as substituents, apart from hydrogen, for example fluorine, chlorine, bromine, iodine, cyano, nitro, methyl, ethyl, isopropyl, tert-butyl, methoxy, ethoxy, isopropoxy, tert-butoxy, trifluoromethyl, chloromethyl, dichloromethyl, trichloromethyl, trifluoromethoxy, 1,1,2,2-tetrafluoroethoxy, methoximinomethyl, ethoximinomethyl, n-propoximinomethyl, n-butoximinomethyl, n-pentoximinomethyl, n-hexyloximinomethyl, allyloximinomethyl, benzyloximinomethyl, isopropoximinomethyl, isobutoximinomethyl, tert-butoximinomethyl, methylimino-1-ethyl, ethoximino-1-ethyl, n-propoximino-1-ethyl, n-butoximino-1-ethyl, n-pentoximino-1-ethyl, n-hexoximino-1-ethyl, allyloximino-1-ethyl, benzyloximino-1-ethyl, phenyl, phenoxy, benzyl, benzyloxy, imidazol-1-yl, piperazin-1-yl, 4-morpholinyl, piperidin-1-yl, pyridyl-2-oxy, cyclopropyl, cyclohexyl, oxiranyl, 1,3-dioxan-2-yl, 1,3-dioxan-2-yl, tetrahydropyran-2-yloxy, dimethylamino, diethylamino, CO$_2$Me, CO$_2$Et, formyl or acyl, Me being methyl and Et being ethyl.

The compounds of the general formula I

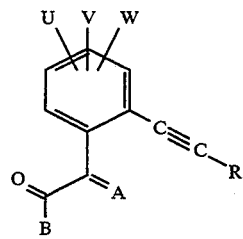

where

U, V and W are each hydrogen,

A is ethylidene, methoxymethylidene or methoximino,

B is methoxy or methylamine and

R has the abovementioned meanings, are preferred.

Owing to the C=C or C=N double bonds, the novel compounds of the general formula I may be obtained in the preparation as E/Z isomer mixtures. These can be separated into the individual components in a conventional manner, for example by crystallization or chromatography. Both the individual isomeric compounds and mixtures thereof form subjects of the invention and can be used as pesticides.

The compounds of the general formula I as claimed in claim 1 are prepared, for example, as described in the following schemes:

The novel compounds of the general formula I can be prepared by reacting, for example, an o-bromo compound 2 with a terminal acetylene derivative 3 in the presence of a transition metal catalyst, preferably a palladium compound, e.g. Pd(PPh$_3$)$_4$, PdCl$_2$ or Pd(OAc)$_2$, in the presence of triphenylphosphine and in the presence of a base, for example an N-alkylamine, such as triethylamine, and in the presence or absence of a solvent or diluent, e.g. dimethylformamide or acetonitrile (cf. for example L. Brandsma et al., Synth. Comm. 20 (1990), 1889 and W. B. Austin et al., J. Org. Chem. 46 (1981), 2280).

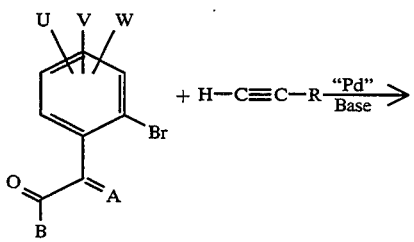

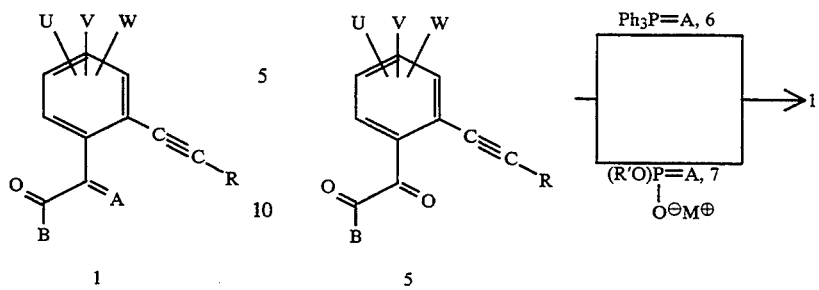

A, B, R, U, V and W have the meanings stated in claim 1.

Alternatively, the compounds of the general formula 1 are obtained by reacting the o-bromo-α-keto acid derivatives 4 with the acetylenes of the formula 3 (conditions similar to Scheme 1)

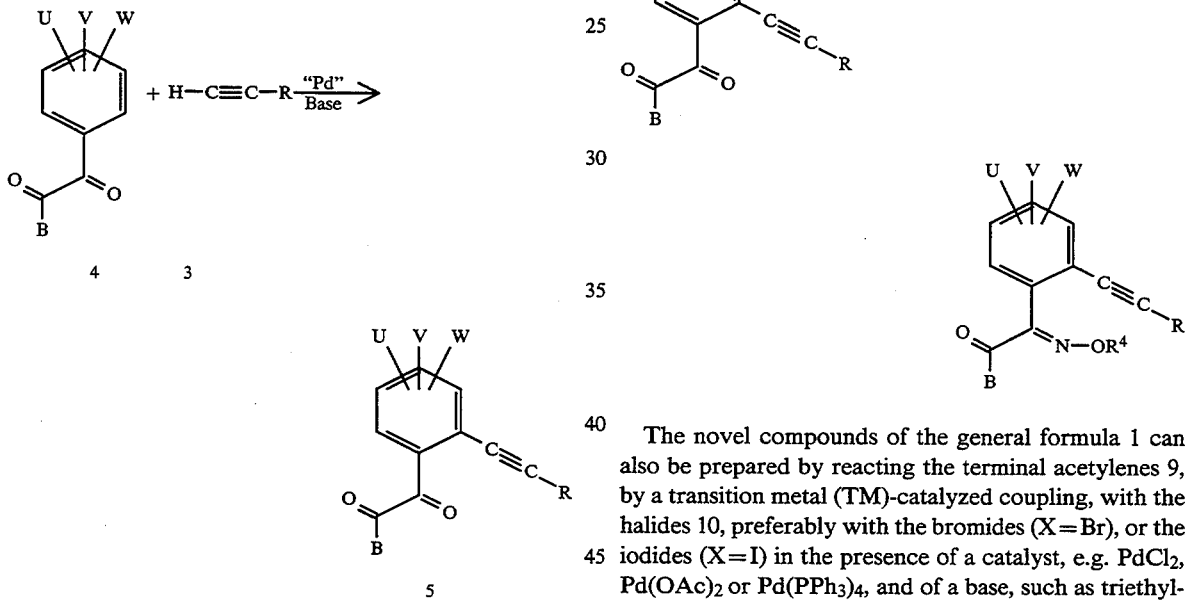

and then reacting the resulting α-ketocarboxylic acid derivatives 5 a) for example in a Wittig or a Wittig-Horner-Emmons reaction with a phosphonium ylide 6 or with a phosphonic acid derivative 7 (Scheme 3) to give the novel compounds of the formula 1, where B, U, V, W and R have the meanings stated in claim 1 and A is CH-alkyl, CH-alkoxy or CH-thioalkyl (cf. for example C. Ferri, Reaktionen der organischen Synthese, Thieme Verlag, Stuttgart, page 354 et seq., 1978), or R'=CH$_3$, M$^\oplus$=alkali metal ion Scheme 3 b) with an O-alkylhydroxylamine 8, in the presence or absence of an acid, e.g. hydrochloric acid, or of a bse, e.g. K$_2$CO$_3$, to give the novel compounds of the formula 1 in which B, U, V, W, R and R$^4$ have the meanings stated in claim 1 (cf. for example European Patent 253,213).

The novel compounds of the general formula 1 can also be prepared by reacting the terminal acetylenes 9, by a transition metal (TM)-catalyzed coupling, with the halides 10, preferably with the bromides (X=Br), or the iodides (X=I) in the presence of a catalyst, e.g. PdCl$_2$, Pd(OAc)$_2$ or Pd(PPh$_3$)$_4$, and of a base, such as triethylamine (cf. for example P. C. Vollhardt, Angew. Chem. 98 (1986), 268 and H. Yamanaka, Synthesis (1983), 312).
Scheme 5

A, B, R, U, V and W have the meanings stated in claim 1.

In an alternative procedure, the α-keto acid derivatives of the terminal acetylenes 11 can be converted with the halides 10 under transition metal

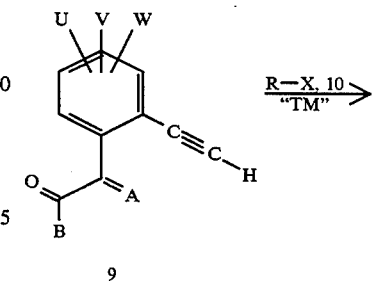

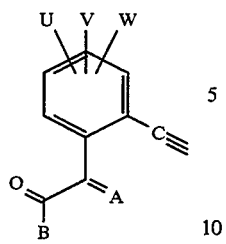

(TM)-catalysis into the derivatives 5, and the latter can be converted as described above into the novel compounds of the formula 1.

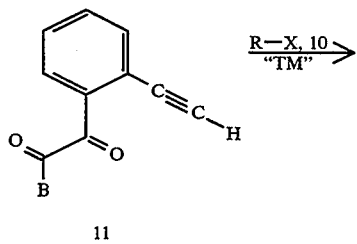

In a further possible method for the preparation of the compounds of the general formula 1, the acetylene group in formula 12 is first produced by a known method (cf. for example Houben-Weyl, Vol. V/2a, page 33 et seq. (Viehe) or see Schemes 1+2)

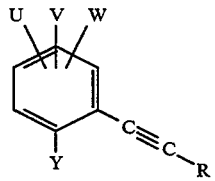

and the group Y is then converted into the group

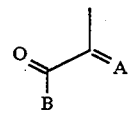

Schemes 7–9 are intended to illustrate this. The keto-carboxylic esters 17 can be prepared starting from the o-bromobenzaldehydes 13.

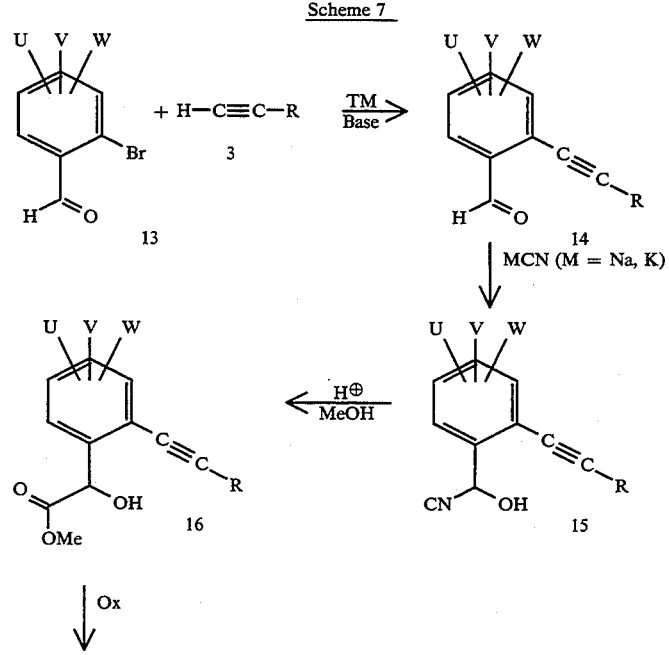

Scheme 7

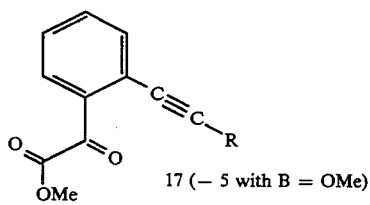

17 (= 5 with B = OMe)

The o-bromobenzaldehydes 12 can be reacted with the terminal acetylenes 3 under transition metal catalysis to give the aldehydes 14 (cf. W. B. Austin, J. Org. Chem. 46 (1981), 2280).

The cyanohydrins 15 are obtained from the aldehydes 14 by reaction with a metal cyanide, such as NaCN or KCN, in the presence of an acid, e.g. hydrochloric acid (cf. for example Organikum, 16th Edition, page 445 (1986)).

The mandelic acid derivatives 16 can be prepared from the cyanohydrins 15 via a Pinner reaction (cf., for example, Org. Synth. Coll. 4 (1963), 58).

Oxidation of the mandelic acid derivatives 16, for example with a chromium compound, such as chromium trioxide, with sodium hypochlorite or with TEMPO gives the α-ketoesters 17 (cf. for example Houben-Weyl, Vol. 4/lb, pages 425–464 (1975); TEMPO = tetramethylpiperidin-1-oxyl).

The novel compounds of the formula 1a, in which A, U, V, W and R have the meanings stated in claim 1 and B is CO2Me, can be prepared from the ketoesters 17, as shown in Schemes 3 and 4. The α-ketocarboxylic esters 17 can be synthesized starting from the halogen derivatives 18, by Grignard reaction with oxalic acid compounds 19 similarly to Scheme 8 (cf., for example, J. S. Nimitz, J. Org. Chem. 46 (1981), 211).

Scheme 8

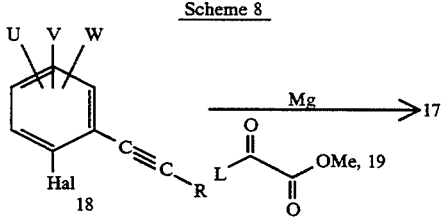

In a further possible method, carboxylic acids 20 are converted via the stage of the acyl chlorides into the cyanides 21 and the latter are converted into the ketoesters 17 by a Pinner reaction.

Scheme 9

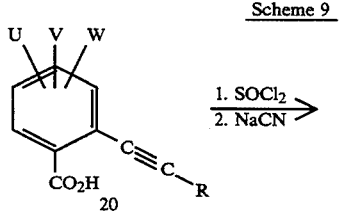

-continued
Scheme 9

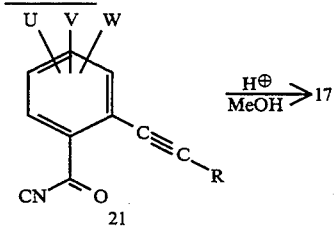

(cf. for example Organikum, 16th Edition, 423 et seq. (1986) and Angew. Chem. 94 (1982), 1).

The novel compounds of the formula 1 where A, X, Y, Z and R have the meanings stated in claim 1 and B is hydroxyl or alkylamino can be prepared from the carboxylic ester derivatives 1a.

Scheme 10

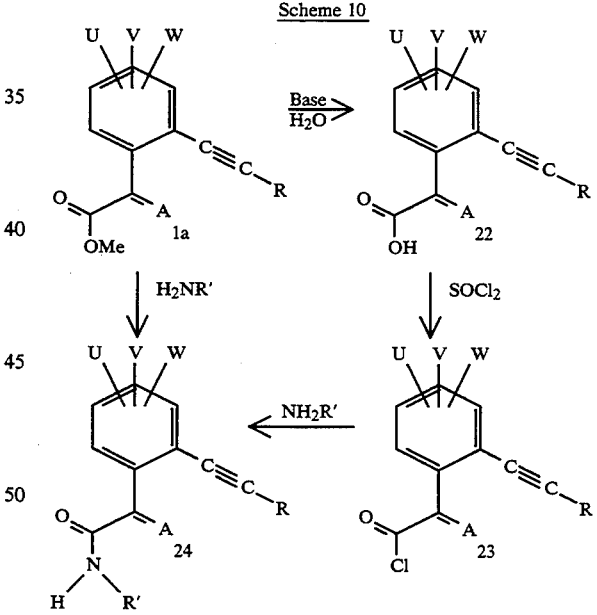

The carboxylic acids 22 are obtained by hydrolysis by known methods (cf. Organikum, 16th Edition, page 415 et seq. and page 622 (1986)).

They can be converted into the acyl chlorides 23 (cf. Organikum, 16th Edition, page 423 et seq. (1986)).

The amides 24 are either obtained from these in a conventional manner (Organikum, 16th Edition, page 412 (1986)) or alternatively from the carboxylic esters 1a directly by aminolysis with amines.

However, the novel compounds of the general formula I can also be prepared by converting a suitably substituted styryl compound 25 in a conventional manner into the corresponding acetylene derivative 1.

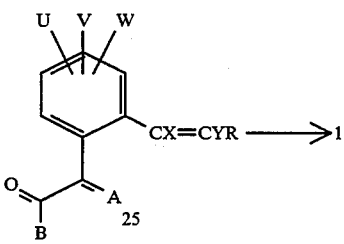

Where X is H and Y is halogen or X is halogen and Y is H, the reaction is carried out in the presence of a base, e.g. sodium hydride, potassium hydroxide, Triton B or n-butyllithium (cf. for example H. Zimmer et al., Chimia 28 (1974), page 656 et seq.) (Triton B=2-benzyltrimethylammonium hydroxide).

Where X and Y are each halogen, the cleavage can be carried out with zinc (cf. for example H. G. Viehe, Chemistry of Acetylenes, Marcel Dekker, New York, 1969, page 134 et seq.).

The Examples which follow illustrate the preparation of the compounds.

EXAMPLES

Example 1

Preparation of methyl 2-ethynylphenylglyoxylate O-methyloxime (compound 1, Table 2)

33.3 g (0.35 mol) of trimethylsilylacetylene, 3.8 g of palladium(II) acetate, 3.2 g of copper(I) iodide and 8.9 g of triphenylphosphine are added to a solution of 55.4 g (0.23 mol) of methyl 2-bromophenylglyoxylate in 415 ml of triethylamine, and nitrogen is then passed through the solution for 30 minutes. The reaction mixture is then heated at 90° C. for 45 minutes, is allowed to cool and is filtered off. The filtrate is evaporated down, the residue is taken up in ethyl acetate and the solution is washed with water. The organic phase is dried and evaporated down. 56.8 g of α-ketoester remain as a black oil.

The crude product prepared in this manner is dissolved in 50 ml of methanol, 38.9 g (0.37 mol) of O-methylhydroxylamine hydrochloride are added and heating is carried out for 15 minutes at 60° C. The mixture is evaporated down, the residue is taken up in ethyl acetate and the solution is washed with water. The organic phase is dried and evaporated down. 52.4 g of compound No. 2 (Table 2) remain as a black oil. $^1$H-NMR (CDCl$_3$/TMS): δ=0.22 (s, 9H, SiMe$_3$); 3.86; 4.06 (s, 3H, OCH$_3$); 7.25–7.61 ppm (m, 4H, aryl).

The trimethylsilylacetylene compound prepared in this manner is dissolved in 320 ml of methanol and stirred together with 3.2 g of potassium carbonate for 1 hour at room temperature (20° C.). The mixture is then evaporated down, the residue is taken up in methylene chloride and the solution is washed with 10% strength sodium bicarbonate solution. The organic phase is dried and evaporated down. 36 g (72%, based on methyl 2-bromophenylglyoxylate) of compound 1 (Table 2) remain as a black solid. $^1$H-NMR (CDCl$_3$/TMS): δ=3.17 (s, 3H, ≡C—H); 3.87; 4.07 (s, 3H, OCH$_3$); 7.27–7.60 ppm (m, 4H, aryl).

Example 2 a) Preparation of methyl 2-(2-methylphenyl)-ethynylphenylglyoxylate O-methyloxime (European Patent 253,213, No. 136)

300 mg of palladium(II) acetate, 1.5 g of triphenylphosphine and 100 mg of copper(I) iodide and 11 g (0.095 mol) of 2-methylphenylacetylene are added to a solution of 10 g (0.041 mol) of methyl 2-bromophenylglyoxylate in 50 ml of triethylamine. Nitrogen is passed through the solution for 30 minutes, after which the solution is heated for 3 hours at 80° C. After cooling, methylene chloride is added and the solution is washed with water. The organic phase is dried and evaporated down. 16.5 g of methyl 2-(2-methylphenyl)-ethynylphenylglyoxylate remain as a black oil. $^1$H-NMR (CDCl$_3$/TMS): δ=2.53 (s, 3H, CH$_3$); 3.81 (s, 3H, OCH$_3$); 7.13–7.88 ppm (m, 8H, aryl).

7.4 g (0.089 mol) of methoxyamine hydrochloride are added to the ketoester obtained in this manner, in 20 ml of methanol, and refluxing is carried out for 1.5 hours. The mixture is evaporated down, the residue is taken up in ethyl acetate, the solution is washed with water and the organic phase is dried and evaporated down. 9.5 g of the product remain as a black oil, which can be recrystallized from methanol. The abovementioned compound is obtained in this manner as a colorless solid having a melting point of 92°–96° C. $^1$H-NMR (CDCl$_3$/TMS): δ=2.46 (s, 3H, CH$_3$); 3.83; 4.07 (s, 3H, OCH$_3$); 7.12–7.63 ppm (m, 8H, aryl).

b) N-Methyl-2-(2-methylphenylethynyl)-phenylglyoxylamide O-methyloxime (compound 32, Table 4)

2 g (7 mmol) of the compound prepared in Example 2a are added to 50 ml of a 40% strength methylamine solution and the mixture is stirred overnight at room temperature. Extraction with ether, drying and evaporation are then carried out. 0.9 g (42%) of compound 32 (Table 4) remains as a pale yellow solid of melting point 128°–129° C. $^1$H-NMR (CDCl$_3$/TMS): δ=2.43 (s, 3H, CH$_3$); 2.91 (d, 3H, NCH$_3$); 3.96 (s, 3H, OCH$_3$); 6.75 (br, 1H, NH); 7.14–7.63 ppm (m, 8H, aryl).

Example 3

Methyl 2-(2-(3-chloro)thienylethynyl)-phenylglyoxylate O-methyloxime (compound 178, Table 2)

100 mg of palladium(II) acetate, 87 mg of copper(I) iodide and 240 mg of triphenylphosphine are added to a solution of 2 g (0.009 mol) of methyl 2-ethynylphenylglyoxylate O-methyl oxime (Example 1) and 3.6 g (0.018 mol) of 2-bromo-3-chlorothiophene in 100 ml of triethylamine. Nitrogen is passed through the solution for 30 minutes, after which the solution is heated for 1 hour at 90° C. The solid formed is filtered off and the filtrate is evaporated down. The residue is taken up in ethyl acetate, the solution is washed with water and the organic phase is dried and evaporated down.

The remaining crude product is chromatographed over silica gel using hexane/methyl tert-butyl ether.

As the first fraction, 700 mg (23%) of compound 178 (Table 2) are obtained in the form of a brown oil. $^1$H-NMR (CDCl$_3$/TMS): δ=3.88; 4.09 (s, 3H, OCH$_3$); 6.93 (d, 1H, =CH); 7.25 (d, 1H, =CH); 7.27–7.66 ppm (m, 4H, aryl).

500 mg (13%) of dimeric starting material are obtained as the second fraction (compound 162, Table 2). $^1$H-NMR (CDCl$_3$/TMS): δ=3.91; 4.09 (s, 3H, OCH$_3$); 7.27–7.61 ppm (m, 4H, aryl).

2. Method 1: Methyl α-[2-(phenylethynyl)-phenyl]-β-methylacrylate [European Patent 280,185, No. 136]

300 mg of palladium(II) acetate, 1.5 g of triphenylphosphine and 100 mg of copper(I) iodide are added to a solution of 10 g (0.041 mol) of methyl 2-bromophenylglyoxylate and 6.3 g (0.061 mol) of phenylacetylene in 50 ml of triethylamine. Nitrogen is passed through the solution for 30 minutes, after which the solution is heated for 90 minutes at 90° C. It is then evaporated down and the residue is taken up in methylene chloride. The solution is washed with water, dried and evaporated down. The remaining residue is chromatographed over silica gel using hexane/methyl tert-butyl ether. 5.5 g of α-ketoester remain as a brown oil after evaporating down. $^1$H-NMR (CDCl$_3$/TMS): δ=2.82 (s, 3H, CH$_3$); 7.36–7.88 ppm (m, 9H, aryl).

2.4 g (0.021 mol) of potassium tert-butylate are added at 5° C. to a solution of 8.7 g (0.021 mol) of ethyltriphenylphosphonium iodide in 60 ml of dry tetrahydrofuran. Stirring is carried out for 1 hour at this temperature, after which a solution of 5.5 g (0.021 mol) of α-ketoester (see above) in 20 ml of tetrahydrofuran is added dropwise at 5° C. and stirring is continued for 3 hours at room temperature. The reaction batch is poured onto water and extracted with methylene chloride, and the organic phase is dried and evaporated down. Chromatography over silica gel using hexane/methyl tert-butyl ether gives 1.2 g of the compound [European Patent 280,185, No. 136] as a brown oil in the form of an E/Z mixture. $^1$H-NMR (CDCl$_3$/TMS): δ=1.74 (d, 3H, CH$_3$-isomer A); 2.22 (d, 3H, CH$_3$-isomer B); 3.70; 3.71 (s, 3H, CH$_3$-isomer A, B); 6.38 (q, 1H, CH); 7.17–7.61 ppm (m, 9H, aryl).

Example 4

Preparation of methyl α-{2-[2-(4-chlorophenyl)-isoxazol-5-ylethynyl]-phenyl}-β-methoxyacrylate (compound 195, Table 1)

0.8 g of methyl α-{2-[2-chloro-2-(3-[4-chlorophenyl]-isoxazol-5-yl)-ethenyl]-phenyl}-β-methoxyacrylate (European Patent 378,755) is dissolved in 10 ml of anhydrous dimethyl sulfoxide, and a pinch of sodium hydride is added. Stirring is carried out overnight at room temperature, and the mixture is poured onto ice water and extracted three times with dichloromethane. The combined organic phases are washed three times with water, dried over sodium sulfate and then evaporated down in a rotary evaporator. The residue is triturated with diisopropyl ether. 0.3 g of the title compound is obtained as colorless crystals of melting point 107°–110° C. $^1$H-NMR (CDCl$_3$/TMS), δ=3.7 (s, 3H); 3.85 (s, 3H); 6.7 (s, 1H); 7.2–7.8 (m, 9H).

Example 5

Preparation of 2-ethynylphenylglyoxylic acid-N-methylamide-O-methyloxime 1 g (4.6 mmol) of the acetylene compound prepared in Example 1 is added to 20 ml of a 40% strength methylamine solution, and the mixture is stirred for 45 minutes at 40°–50° C. The solution is extracted with methyl tert-butyl ether, dried and evaporated down. 700 mg (70%) of the compound remain as a colorless solid.

$^1$H-NMR (CDCl$_3$/TMS): δ=2.99 (d, 2H, NCH$_3$); 3.13 (s, 1H, ≡C—H), 3.98 (s, 3H, OCH$_3$), 6.80 (br, 1H, NH); 7.21–7.58 ppm (m, 4H).

Example 6

Preparation of methyl 2-benzoyl-ethynylphenylglyoxylate O-methyloxime (compound 26, Table 6)

Under a nitrogen blanket and at 90° C., 2 g (9.2 mmol) of the acetylene derivative from Example 1 is added to a mixture of 50 mg of copper(II) chloride, 110 mg of palladium(II) acetate, 380 mg of triphenylphosphine and 2.6 g (18.4 mmol) of benzoyl chloride in 100 ml of triethylamine. After 30 minutes, the mixture is allowed to cool and the solid is filtered off. The filtrate is evaporaed down, and the residue is taken up in methyl tert-butyl ether, washed with water, dried and evaporated down. The residue is stirred with diethyl ether and the precipitated pale brown solid is filtered off. 2.0 g (68%) of compound 26, Table 6, remain. Mp. 89°–94° C.

Example 7

Preparation of methyl 2-(methoxyiminobenzoyl)ethynylphenylglyoxylate O-methyloxime (compound 10, Table 9).

A mixture of 1.5 g (4.7 mmol) of compound 26 from Table 6 (from Example 6) and 2.6 g of O-methylhydroxylamine hydrochloride in 5 ml of methanol is heated for 90 min at 60° C. The mixture is evaporated down and the residue is taken up in methyl tert-butyl ether and washed with water, followed by drying and evaporating down. The residue is chromatographed on silica gel using mixtures of methyl tert-butyl ether and hexane. 1.1 g (67%) of compound 10 from Table 9 remain as a yellow oil (isomer mixture).

$^1$H-NMR (CDCl$_3$/TMS): δ=3.81; 4.04; 4.12 (3H, OCH$_3$); 7.28–7.88 ppm (9H).

TABLE 1

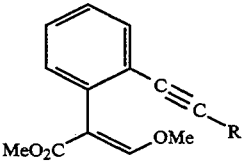

| No. | R | phys. data (m.p. [°C.]); IR [cm$^{-1}$]; $^1$H-NMR [δ scale] |
|-----|---|---|
| 1 | H | |
| 2 | SiMe$_3$ | |
| 3 | S$_n$Me$_3$ | |
| 4 | I | |
| 5 | CN | |
| 6 | CH$_3$ | |
| 7 | CH$_2$CH$_3$ | |
| 8 | n-C$_3$H$_7$ | |
| 9 | i-C$_3$H$_7$ | |
| 10 | n-C$_4$H$_9$ | |
| 11 | i-C$_4$H$_9$ | |
| 12 | s-C$_4$H$_9$ | |
| 13 | t-C$_4$H$_9$ | |
| 14 | n-C$_5$H$_{11}$ | |
| 15 | n-C$_6$H$_{13}$ | |
| 16 | n-C$_7$H$_{15}$ | |
| 17 | n-C$_8$H$_{17}$ | |
| 18 | n-C$_9$H$_{19}$ | |
| 19 | n-C$_{10}$H$_{21}$ | |
| 20 | cyclopropyl | |
| 21 | 1-methyl-cycloprop-1-yl | |
| 22 | cyclobutyl | |
| 23 | cyclopentyl | |
| 24 | cyclohexyl | |
| 25 | cyclohex-1-en-1-yl | |
| 26 | methoxymethyl | |
| 27 | ethoxymethyl | |
| 28 | phenoxymethyl | |
| 29 | benzyloxymethyl | |
| 30 | phenylmethyl | |
| 31 | morpholino-N-methyl | |
| 32 | phenylthiomethyl | |
| 33 | 2-methylphenyl | |
| 34 | 3-methylphenyl | |
| 35 | 4-methylphenyl | |
| 36 | 2-chlorophenyl | |
| 37 | 3-chlorophenyl | |

TABLE 1-continued

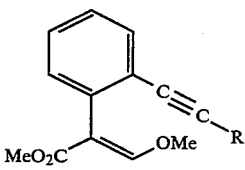

| No. | R | phys. data (m.p. [°C]); IR [cm$^{-1}$]; $^1$H-NMR [δ scale] |
|---|---|---|
| 38 | 4-chlorophenyl | |
| 39 | 2-bromophenyl | |
| 40 | 3-bromophenyl | |
| 41 | 4-bromophenyl | |
| 42 | 2-fluorophenyl | |
| 43 | 3-fluorophenyl | |
| 44 | 4-fluorophenyl | |
| 45 | 2-iodophenyl | |
| 46 | 3-iodophenyl | |
| 47 | 4-iodophenyl | |
| 48 | 2-methoxyphenyl | |
| 49 | 3-methoxyphenyl | |
| 50 | 4-methoxyphenyl | |
| 51 | 2-ethoxyphenyl | |
| 52 | 3-ethoxyphenyl | |
| 53 | 4-ethoxyphenyl | |
| 54 | 2-n-propoxyphenyl | |
| 55 | 3-n-propoxyphenyl | |
| 56 | 4-n-propoxyphenyl | |
| 57 | 2-i-propoxyphenyl | |
| 58 | 3-i-propoxyphenyl | |
| 59 | 4-i-propoxyphenyl | |
| 60 | 2-n-butoxyphenyl | |
| 61 | 3-n-butoxyphenyl | |
| 62 | 4-n-butoxyphenyl | |
| 63 | 2-sec.-butoxyphenyl | |
| 64 | 3-sec.-butoxyphenyl | |
| 65 | 4-sec.-butoxyphenyl | |
| 66 | 2-iso-butoxyphenyl | |
| 67 | 3-isobutoxyphenyl | |
| 68 | 4-isobutoxyphenyl | |
| 69 | 2-tert.-butoxyphenyl | |
| 70 | 3-tert.-butoxyphenyl | |
| 71 | 4-tert.-butoxyphenyl | |
| 72 | 2-ethylphenyl | |
| 73 | 3-ethylphenyl | |
| 74 | 4-ethylphenyl | |
| 75 | 2-n-propylphenyl | |
| 76 | 3-n-propylphenyl | |
| 77 | 4-n-propylphenyl | |
| 78 | 2-i-propylphenyl | |
| 79 | 3-i-propylphenyl | |
| 80 | 4-i-propylphenyl | |
| 81 | 2-n-butylphenyl | |
| 82 | 3-n-butylphenyl | |
| 83 | 4-n-butylphenyl | |
| 84 | 2-isobutylphenyl | |
| 85 | 3-isobutylphenyl | |
| 86 | 4-isobutylphenyl | |
| 87 | 2-sec.-butylphenyl | |
| 88 | 3-sec.-butylphenyl | |
| 89 | 4-sec.-butylphenyl | |
| 90 | 2-tert.-butylphenyl | |
| 91 | 3-tert.-butylphenyl | |
| 92 | 4-tert.-butylphenyl | |
| 93 | 2-NO$_2$-phenyl | |
| 94 | 3-NO$_2$-phenyl | |
| 95 | 4-NO$_2$-phenyl | |
| 96 | 2-CF$_3$-phenyl | |
| 97 | 3-CF$_3$-phenyl | |
| 98 | 4-CF$_3$-phenyl | |
| 99 | 2-CN-phenyl | |
| 100 | 3-CN-phenyl | |
| 101 | 4-CN-phenyl | |
| 102 | 2-(CH$_2$C≡N)-phenyl | |
| 103 | 3-(CH$_2$C≡N)-phenyl | |
| 104 | 4-(CH$_2$C≡N)-phenyl | |
| 105 | 2-CH$_3$CO-phenyl | |
| 106 | 3-CH$_3$CO-phenyl | |

TABLE 1-continued

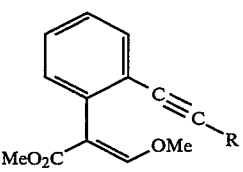

| No. | R | phys. data (m.p. [°C]); IR [cm$^{-1}$]; $^1$H-NMR [δ scale] |
|---|---|---|
| 107 | 4-CH$_3$CO-phenyl | |
| 108 | 2-CHO-phenyl | |
| 109 | 3-CHO-phenyl | |
| 110 | 4-CHO-phenyl | |
| 111 | 2-NMe$_2$-phenyl | |
| 112 | 3-NMe$_2$-phenyl | |
| 113 | 4-NMe$_2$-phenyl | |
| 114 | 2-CO$_2$Me-phenyl | |
| 115 | 3-CO$_2$Me-phenyl | |
| 116 | 4-CO$_2$Me-phenyl | |
| 117 | 2-CO$_2$Et-phenyl | |
| 118 | 3-CO$_2$Et-phenyl | |
| 119 | 4-CO$_2$Et-phenyl | |
| 120 | 2-OCF$_3$-phenyl | |
| 121 | 3-OCF$_3$-phenyl | |
| 122 | 4-OCF$_3$-phenyl | |
| 123 | 2-phenyl-phenyl | |
| 124 | 3-phenyl-phenyl | |
| 125 | 4-phenyl-phenyl | |
| 126 | 2-phenoxy-phenyl | |
| 127 | 3-phenoxy-phenyl | |
| 128 | 4-phenoxy-phenyl | |
| 129 | 3,4-OCH$_2$O-phenyl | |
| 130 | 3,4-OCH$_2$CH$_2$-phenyl | |
| 131 | 3,4,5-(OCH$_3$)$_3$-phenyl | |
| 132 | 3,4-(OCH$_3$)$_2$-phenyl | |
| 133 | 2,3-Me$_2$-phenyl | |
| 134 | 2,4-Me$_2$-phenyl | |
| 135 | 2,5-Me$_2$-phenyl | |
| 136 | 2,6-Me$_2$-phenyl | |
| 137 | 3,4-Me$_2$-phenyl | |
| 138 | 3,5-Me$_2$-phenyl | |
| 139 | 2,4,6-Me$_3$-phenyl | |
| 140 | 2,3-Cl$_2$-phenyl | |
| 141 | 2,4-Cl$_2$-phenyl | |
| 142 | 2,5-Cl$_2$-phenyl | |
| 143 | 2,6-Cl$_2$-phenyl | |
| 144 | 3,4-Cl$_2$-phenyl | |
| 145 | 3,5-Cl$_2$-phenyl | |
| 146 | 2-methyl, 5-NO$_2$-phenyl | |
| 147 | 2-methyl, 3-NO$_2$-phenyl | |
| 148 | 2-methyl, 4-F-phenyl | |
| 149 | 4-methyl, 3-F-phenyl | |
| 150 | 2,6-Cl$_2$, 4-NO$_2$-phenyl | |
| 151 | 2-NO$_2$, 4-Cl-phenyl | |
| 152 | 2-Cl, 5-CF$_3$-phenyl | |
| 153 | 4-Cl, 3-CF$_3$-phenyl | |
| 154 | 2-methyl, 4-CH$_3$CO-phenyl | |
| 155 | 2-methyl, 5-CH$_3$CO-phenyl | |
| 156 | 2,5-Me$_2$, 4-CH$_3$CO-phenyl | |
| 157 | 2-Me, 4-methoximinomethyl-phenyl | |
| 158 | 2-Me, 5-methoximinomethyl-phenyl | |
| 159 | 2,5-Me$_2$, 4-methoximinomethyl-phenyl | |
| 160 | 2-Me, 4-ethoximinomethyl-phenyl | |
| 161 | 2-Me, 4-n-propoximinomethyl-phenyl | |
| 162 | 2-Me, 4-i-propoximinomethyl-phenyl | |
| 163 | 2-Me, 4-n-butoximinomethyl-phenyl | |
| 164 | 2-Me, 5-ethoximinomethyl-phenyl | |
| 165 | 2,5-Me$_2$, 4-ethoximinomethylphenyl | |
| 166 | 3-(5-phenyl-1,3,4-oxadiazol-2-yl)-phenyl | |
| 167 | 3-(5-naphthyl-1,3,4-oxadiazol-2-yl)-phenyl | |
| 168 | 2-pyridyl | |
| 169 | 3-pyridyl | |
| 170 | 4-pyridyl | |
| 171 | 5-methyl-2-pyridyl | |
| 172 | 6-methyl-2-pyridyl | |
| 173 | quinolin-3-yl | |

TABLE 1-continued

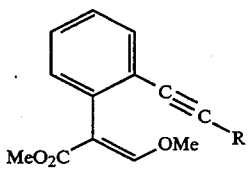

| No. | R | phys. data (m.p. [°C.]); IR [cm⁻¹]; $^1$H-NMR [δ scale] |
|---|---|---|
| 174 | 2,8(CF$_3$)$_2$-quinolin-4-yl | |
| 175 | Isoquinolin-4-yl | |
| 176 | thien-2-yl | |
| 177 | thien-3-yl | |
| 178 | 2-chloro-thien-3-yl | |
| 179 | 2-chloro-thien-4-yl | |
| 180 | 3-chloro-thien-2-yl | |
| 181 | 2-chloro-thien-5-yl | |
| 182 | 2,5-Cl$_2$-thien-3-yl | |
| 183 | 3-furyl | |
| 184 | 2-(isoxazol-3-yl)-thien-5-yl | |
| 185 | 2-cyano-thien-3-yl | |
| 186 | 3-Me-thien-2-yl | |
| 187 | 2-NO$_2$-thien-5-yl | |
| 188 | 3-benzothienyl | |
| 189 | 3,5-Me$_2$-isoxazol-3-yl | |
| 190 | 2-thiazolyl | |
| 191 | 5-NO$_2$-thiazol-2-yl | |
| 192 | 5-NO$_2$-imidazol-4-yl | |
| 193 | 4-pyrrazolyl | |
| 194 | 3,5-Me$_2$-pyrrazol-4-yl | |
| 195 | 3-(4-Cl-phenyl)-isoxazol-5-yl | 107–110° C. |
| 196 | 4-chloro-3-(3-chlorophenyl)-isoxazol-5-yl | |
| 197 | 5-(4-methylphenyl)-1,3,4-oxadiazol-2-yl | |
| 198 | 5-phenyl-1,3,4-thiadiazol-2-yl | |
| 199 | 3-(4-chlorophenyl)-1,2,4-oxadiazol-5-yl | |
| 200 | 3-isopropyl-isoxazol-5-yl | |
| 201 | 5-(4-F-phenyl)-isoxazol-3-yl | |
| 202 | 4-ethyl-5-phenyl-isoxazol-3-yl | |
| 203 | 4-chloro-5-(3-Cl-phenyl)-isoxazol-3-yl | |
| 204 | CH$_2$Br | |
| 205 | CH$_2$Cl | |
| 206 | CH$_2$I | |
| 207 | 1-naphthyl | |
| 208 | 2-naphthyl | |
| 209 | 6-methoxy-napht-2-yl | |

TABLE 2

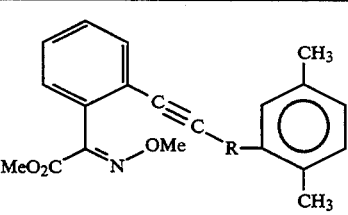

| No. | R | phys. data (m.p. [°C.]); IR [cm⁻¹]; $^1$H-NMR [δ scale] |
|---|---|---|
| 1 | H | 3.17 (CH); 3.87; 4.07 (Me); 7.27–7.60 (aryl) |
| 2 | SiMe$_3$ | 0.22; 3.86; 4.06 (Me); 7.25–7.61 (aryl) |
| 3 | SnMe$_3$ | |

TABLE 2-continued

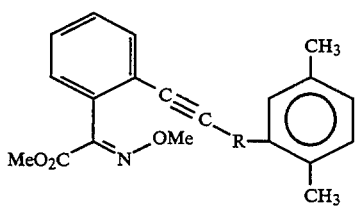

| No. | R | phys. data (m.p. [°C.]); IR [cm⁻¹]; $^1$H-NMR [δ scale] |
|---|---|---|
| 4 | I | |
| 5 | CN | |
| 6 | CH$_3$ | |
| 7 | CH$_2$CH$_3$ | |
| 8 | n-C$_3$H$_7$ | |
| 9 | i-C$_3$H$_7$ | |
| 10 | n-C$_4$H$_9$ | |
| 11 | i-C$_4$H$_9$ | |
| 12 | s-C$_4$H$_9$ | |
| 13 | t-C$_4$H$_9$ | |
| 14 | n-C$_5$H$_{11}$ | |
| 15 | n-C$_6$H$_{13}$ | |
| 16 | n-C$_7$H$_{15}$ | |
| 17 | n-C$_8$H$_{17}$ | |
| 18 | n-C$_9$H$_{19}$ | |
| 19 | n-C$_{10}$H$_{21}$ | |
| 20 | cyclopropyl | |
| 21 | 1-methyl-cycloprop-1-yl | |
| 22 | cyclobutyl | |
| 23 | cyclopentyl | |
| 24 | cyclohexyl | 1.23–2.61 (cyclohexyl); 3.85; 4.05 (Me); 7.22–7.48 (aryl) |
| 25 | cyclohex-1-en-1-yl | 98–100° C. |
| 26 | methoxymethyl | 3.41; 3.87; 4.07 (Me); 4.28 (CH$_2$); 7.28–7.55 (aryl) |
| 27 | ethoxymethyl | |
| 28 | phenoxymethyl | |
| 29 | benzyloxymethyl | |
| 30 | phenylmethyl | |
| 31 | morpholino-N-methyl | 2.59; 3.49; 3.76 (CH$_2$); 3.87; 4.07 (Me); 7.23–7.71 (aryl) |
| 32 | phenylthiomethyl | |
| 33 | 3-methyl-phenyl | 95–99° C. |
| 34 | 3-chloro-phenyl | 3.86; 4.09 (Me); 7.25–7.63 (aryl) |
| 35 | 4-chloro-phenyl | 91–96° C. |
| 36 | 3-bromo-phenyl | |
| 37 | 3-fluorophenyl | |
| 38 | 4-fluorophenyl | |
| 39 | 2-iodo-phenyl | |
| 40 | 3-iodo-phenyl | |
| 41 | 4-iodo-phenyl | |
| 42 | 3-methoxy-phenyl | 3.82; 3.84; 4.08 (Me); 6.87–7.63 (aryl) |
| 43 | 4-methoxy-phenyl | 118–121° C. |
| 44 | 2-ethoxy-phenyl | |
| 45 | 3-ethoxy-phenyl | |
| 46 | 4-ethoxy-phenyl | 1.42; 3.84; 4.07 (Me); 4.05 (CH$_2$); 6.84–7.61 (aryl) |
| 47 | 2-n-propoxy-phenyl | |
| 48 | 3-n-propoxy-phenyl | |
| 49 | 4-n-propoxy-phenyl | |
| 50 | 2-i-propoxy-phenyl | |
| 51 | 3-i-propoxy-phenyl | 1.34; 3.87; 4.08 (Me); 4.57 (CH); 6.75– |

TABLE 2-continued

Structure: 2-position of benzene ring has C≡C-C(R)(OMe) linked to a 2,6-dimethylphenyl group; 1-position has MeO$_2$C-C=N-OMe group.

| No. | R | phys. data (m.p. [°C.]); IR [cm$^{-1}$]; $^1$H-NMR [δ scale] |
|---|---|---|
| 52 | 4-i-propoxy-phenyl | 7.61 (aryl) |
| 53 | 2-n-butoxy-phenyl | |
| 54 | 3-n-butoxy-phenyl | |
| 55 | 4-n-butoxy-phenyl | |
| 56 | 2-sec.-butoxy-phenyl | |
| 57 | 3-sec.-butoxy-phenyl | |
| 58 | 4-sec.-butoxy-phenyl | |
| 59 | 2-iso-butoxy-phenyl | |
| 60 | 3-iso-butoxy-phenyl | |
| 61 | 4-iso-butoxy-phenyl | |
| 62 | 2-tert.-butoxyphenyl | |
| 63 | 3-tert.-butoxyphenyl | |
| 64 | 4-tert.-butoxyphenyl | |
| 65 | 2-ethyl-phenyl | |
| 66 | 3-ethyl-phenyl | |
| 67 | 4-ethyl-phenyl | 1.23; 3.84; 4.09 (Me); 2.65 (CH$_2$); 7.17–7.63 (aryl) |
| 68 | 2-n-propyl-phenyl | |
| 69 | 3-n-propyl-phenyl | |
| 70 | 4-n-propyl-phenyl | |
| 71 | 2-i-propyl-phenyl | |
| 72 | 3-i-propyl-phenyl | |
| 73 | 4-i-propyl-phenyl | 1.24; 3.85; 4.09 (Me); 2.91 (CH); 7.20–7.61 (aryl) |
| 74 | 2-n-butylphenyl | |
| 75 | 3-n-butylphenyl | |
| 76 | 4-n-butylphenyl | |
| 77 | 2-iso-butyl-phenyl | |
| 78 | 3-iso-butyl-phenyl | |
| 79 | 4-iso-butyl-phenyl | |
| 80 | 2-sec.-butylphenyl | |
| 81 | 3-sec.-butylphenyl | |
| 82 | 4-sec.-butylphenyl | |
| 83 | 2-tert.-butylphenyl | |
| 84 | 3-tert.-butylphenyl | |
| 85 | 4-tert.-butylphenyl | 1.31; 3.85; 4.09 (Me); 7.35–7.61 (aryl) |
| 86 | 3-NO$_2$-phenyl | 122–125° C. |
| 87 | 4-NO$_2$-phenyl | 160–164° C. |
| 88 | 2-CF$_3$-phenyl | 66–70° C. |
| 89 | 3-CF$_3$-phenyl | 3.86; 4.09 (Me); 7.33–7.73 (aryl) |
| 90 | 2-CN-phenyl | |
| 91 | 3-CN-phenyl | |
| 92 | 4-CN-phenyl | 145–149° C. |
| 93 | 2-(CH$_2$C≡N)-phenyl | 3.82; 4.04 (Me); 3.92 (CH$_2$); 7.25–7.65 (aryl) |
| 94 | 3-(CH$_2$C≡N)-phenyl | 3.75 (CH$_2$); 3.84; 4.08 (Me); 7.33–7.63 (aryl) |
| 95 | 4-(CH$_2$C≡N)-phenyl | 85–90° C. |
| 96 | 2-CH$_3$CO-phenyl | |
| 97 | 3-CH$_3$CO-phenyl | |
| 98 | 4-CH$_3$CO-phenyl | 121–123° C. |
| 99 | 2-CHO-phenyl | |
| 100 | 3-CHO-phenyl | 3.87; 4.10 (Me); 7.36–7.94; (aryl; 10.01 (CH) |
| 101 | 4-CHO-phenyl | 104–106° C. |
| 102 | 2-NMe$_2$-phenyl | |
| 103 | 3-NMe$_2$-phenyl | |
| 104 | 4-NMe$_2$-phenyl | 2.99; 3.82; 4.06 (Me); 6.59–7.55 (aryl) |
| 105 | 2-CO$_2$Me-phenyl | |
| 106 | 3-CO$_2$Me-phenyl | 3.86; 3.94; 4.09 (Me); 7.35–8.14 (aryl) |
| 107 | 4-CO$_2$Me-phenyl | |
| 108 | 2-CO$_2$Et-phenyl | |
| 109 | 3-CO$_2$Et-phenyl | |
| 110 | 4-CO$_2$Et-phenyl | |
| 111 | 2-OCF$_3$-phenyl | |
| 112 | 3-OCF$_3$-phenyl | |
| 113 | 4-OCF$_3$-phenyl | |
| 114 | 2-phenyl-phenyl | 3.79; 4.01 (Me); 7.23–7.61 (aryl) |
| 115 | 3-phenyl-phenyl | 3.85; 4.09 (Me); 7.38–7.73 (aryl) |
| 116 | 4-phenyl-phenyl | 137–142° C. |
| 117 | 2-phenoxy-phenyl | |
| 118 | 3-phenoxy-phenyl | |
| 119 | 4-phenoxy-phenyl | 3.82; 4.07 (Me); 6.92–7.58 (aryl) |
| 120 | 3,4-OCH$_2$O-phenyl | 3.84; 4.07 (Me); 5.98 (CH$_2$); 6.76–7.58 (aryl) |
| 121 | 3,4-OCH$_2$CH$_2$O-phenyl | 3.84; 4.07 (Me); 4.25 (CH$_2$); 6.79–7.58 (aryl) |
| 122 | 3,4,5-(OCH$_3$)$_3$-phenyl | 3.86; 3.88; 3.89; 3.92; 4.10 (Me); 6.75–7.61 (aryl) |
| 123 | 3,4-(OCH$_3$)$_2$-phenyl | |
| 124 | 2,3-Me$_2$-phenyl | 105–109° C. |
| 125 | 2,4-Me$_2$-phenyl | 104–109° C. |
| 126 | 2,5-Me$_2$-phenyl | 142–147° C. |
| 127 | 2,6-Me$_2$-phenyl | |
| 128 | 3,4-Me$_2$-phenyl | 86–89° C. |
| 129 | 3,5-Me$_2$-phenyl | 2.30 (2x); 3.84; 4.08 (Me); 6.97–7.61 (aryl) |
| 130 | 2,4,6-Me$_3$-phenyl | 108–112° C. |
| 131 | 2,3-Cl$_2$-phenyl | 117–121° C. |
| 132 | 2,4-Cl$_2$-phenyl | 113–116° C. |
| 133 | 2,5-Cl$_2$-phenyl | 107–110° C. |
| 134 | 2,6-Cl$_2$-phenyl | 145–148° C. |
| 135 | 3,4-Cl$_2$-phenyl | 93–96° C. |
| 136 | 3,5-Cl$_2$-phenyl | 106–109° C. |
| 137 | 2-methyl, 5-NO$_2$-phenyl | |
| 138 | 2-methyl, 3-NO$_2$-phenyl | |
| 139 | 2-methyl, 4-F-phenyl | |
| 140 | 4-methyl, 3-F-phenyl | |
| 141 | 2,6-Cl$_2$, 4-NO$_2$-phenyl | |
| 142 | 2-NO$_2$, 4-Cl-phenyl | |
| 143 | 2-Cl, 5-CF$_3$-phenyl | 3.87; 4.07 (Me); |

TABLE 2-continued

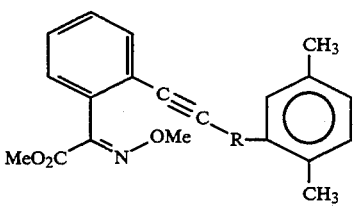

| No. | R | phys. data (m.p. [°C.]); IR [cm⁻¹]; ¹H-NMR [δ scale] |
|---|---|---|
| 144 | 4-Cl, 3-CF₃-phenyl | 7.35–8.37 (aryl) |
| 145 | 2-methyl, 4-CH₃CO-phenyl | |
| 146 | 2-methyl, 5-CH₃CO-phenyl | |
| 147 | 2,5-Me₂, 4-CH₃CO-phenyl | |
| 148 | 2-Me, 4-methoximinomethyl-phenyl | 2.22; 2.46; 3.86; 4.01; 4.09 (Me); 7.20–7.75 (aryl) |
| 149 | 2-Me, 5-methoximinomethyl-phenyl | 2.22; 2.45; 3.84; 3.99; 4.06 (Me); 7.17–7.71 (aryl) |
| 150 | 2,5-Me₂, 4-methoximinomethyl-phenyl | |
| 151 | 2-Me, 4-ethoximinomethyl-phenyl | |
| 152 | 2-Me, 4-n-propoximinomethyl-phenyl | |
| 153 | 2-Me, 4-i-propoximinomethyl-phenyl | |
| 154 | 2-Me, 4-n-butoximinomethyl-phenyl | |
| 155 | 2-Me, 5-ethoximinomethyl-phenyl | |
| 156 | 2,5-Me₂, 4-ethoximinomethyl-phenyl | |
| 157 | 1-Me-2-naphthyl | |
| 158 | 1-naphthyl | 3.82; 4.09 (Me); 7.35–8.37 (aryl) |
| 159 | 2-naphthyl | 114–118° C. |
| 160 | 6-methoxy-2-naphthyl | 3.86; 3.95; 4.11 (Me); 7.12–7.94 (aryl) |
| 161 | 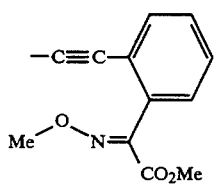 | 2240 (—C≡C—, RA-MAN) |
| 162 | 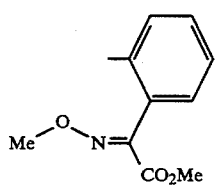 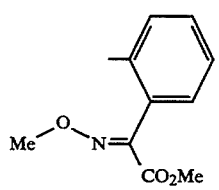 | 1725; 1441; 1258; 1209; 1069; 1037; 1013; 950 |

TABLE 2-continued

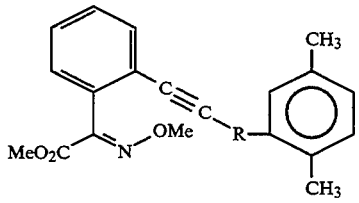

| No. | R | phys. data (m.p. [°C.]); IR [cm⁻¹]; ¹H-NMR [δ scale] |
|---|---|---|
| 163 | (two structures shown with CH₂/MeO₂C/N-OMe groups) | 1727; 1437; 1324; 1309; 1264; 1215; 1069; 1040 |
| 164 | 3-(5-phenyl-1,3,4-oxadiazol-2-yl)-phenyl | 44–52° C. |
| 165 | 3-(5-naphthyl-1,3,4-oxa-diazol-2-yl)-phenyl | |
| 166 | 2-pyridyl | 3.87; 4.09 (Me); 7.22–8.62 (8H) |
| 167 | 3-pyridyl | 78–82° C. |
| 168 | 4-pyridyl | |
| 169 | 5-methyl-2-pyridyl | |
| 170 | 6-methyl-2-pyridyl | |
| 171 | quinolin-3-yl | |
| 172 | 2,8(CF₃)₂-quinolin-4-yl | |
| 173 | isoquinolin-4-yl | |
| 174 | thien-2-yl | 3.87; 4.09 (Me); 6.95–7.58 (aryl) |
| 175 | thien-3-yl | 80–89° C. |
| 176 | 2-chloro-thien-3-yl | |
| 177 | 2-chloro-thien-4-yl | 3.84; 4.07 (Me); 6.98–7.58 (aryl) |
| 178 | 3-chloro-thien-2-yl | 3.88; 4.09 (Me); 6.93–7.66 (aryl) |
| 179 | 2-chloro-thien-5-yl | 3.87; 4.08 (Me); 6.81–7.59 (aryl) |
| 180 | 2,5-Cl₂-thien-3-yl | |
| 181 | 3-furyl | |
| 182 | 2-(isoxazol-3-yl)-thien-5-yl | |
| 183 | 2-cyano-thien-3-yl | |
| 184 | 3-Me-thien-2-yl | |
| 185 | 2-NO₂-thien-5-yl | |
| 186 | 3-benzothienyl | |
| 187 | 3,5-Me₂-isoxazol-3-yl | |
| 188 | 2-thiazolyl | |
| 189 | 5-NO₂-thiazol-2-yl | |
| 190 | 5-NO₂-imidazol-4-yl | |
| 191 | 4-pyrrazolyl | |
| 192 | 3,5-Me₂-pyrrazol-4-yl | |
| 193 | 3-(4-Cl-phenyl)-isoxazol-5-yl | |
| 194 | 4-chloro-3-(3-chlorophenyl)-isoxazol-5-yl | |
| 195 | 5-(4-methylphenyl)-1,3,4-oxadiazol-2-yl | |
| 196 | 5-phenyl-1,3,4-thiadiazol-2-yl | |

TABLE 2-continued

[Structure: 2-alkynyl-phenyl compound with MeO2C-C(=N-OMe)- group, R on 2,6-dimethylphenyl ring]

| No. | R | phys. data (m.p. [°C.]); IR [cm$^{-1}$]; $^1$H-NMR [δ scale] |
|---|---|---|
| 197 | 3-(4-chlorophenyl)-1,2,4-oxadiazol-5-yl | |
| 198 | 3-isopropyl-isoxazol-5-yl | |
| 199 | 5-(4-F-phenyl)-isoxazol-3-yl | |
| 200 | 4-ethyl-5-phenyl-isoxazol-3-yl | |
| 201 | 4-chloro-5-(3-Cl-phenyl)-isoxalzol-3-yl | |
| 202 | CH$_2$Br | |
| 203 | CH$_2$Cl | |
| 204 | CH$_2$I | |
| 205 | 9-anthracenyl | 159–164° C. |
| 206 | 2-methoxy-naphth-1-yl | 129–137° C. |
| 207 | CH=CH-phenyl | 97–102° C. |
| 208 | 4-(benzthiazol-2-yl)-phenyl | 164–168° C. |
| 209 | 1-pyrenyl | 179–183° C. |

TABLE 3

[Structure: 2-alkynyl-phenyl compound with MeO2C-C(=CH-Me)- group, R on alkyne]

| No. | R | phys. data (m.p. [°C.]); IR [cm$^{-1}$]; $^1$H-NMR [δ scale] |
|---|---|---|
| 1 | H | |
| 2 | SiMe$_3$ | |
| 3 | SnMe$_3$ | |
| 4 | I | |
| 5 | CN | |
| 6 | CH$_3$ | |
| 7 | CH$_2$CH$_3$ | |
| 8 | n-C$_3$H$_7$ | |
| 9 | i-C$_3$H$_7$ | |
| 10 | n-C$_4$H$_9$ | |
| 11 | i-C$_4$H$_9$ | |
| 12 | s-C$_4$H$_9$ | |
| 13 | t-C$_4$H$_9$ | |
| 14 | n-C$_5$H$_{11}$ | |
| 15 | n-C$_6$H$_{13}$ | |
| 16 | n-C$_7$H$_{15}$ | |
| 17 | n-C$_8$H$_{17}$ | |
| 18 | n-C$_9$H$_{19}$ | |
| 19 | n-C$_{10}$H$_{21}$ | |
| 20 | cyclopropyl | |
| 21 | 1-methyl-cycloprop-1-yl | |
| 22 | cyclobutyl | |
| 23 | cyclopentyl | |
| 24 | cyclohexyl | |
| 25 | cyclohex-1-en-1-yl | |
| 26 | methoxymethyl | |
| 27 | ethoxymethyl | |
| 28 | phenoxymethyl | |
| 29 | benzyloxymethyl | |
| 30 | phenylmethyl | |
| 31 | morpholino-N-methyl | |
| 32 | phenylthiomethyl | |
| 33 | 3-methyl-phenyl | |
| 34 | 3-chloro-phenyl | |
| 35 | 4-chloro-phenyl | |
| 36 | 3-bromo-phenyl | |
| 37 | 3-fluorophenyl | |
| 38 | 4-fluorophenyl | |
| 39 | 2-iodo-phenyl | |
| 40 | 3-iodo-phenyl | |
| 41 | 4-iodo-phenyl | |
| 42 | 3-methoxy-phenyl | |
| 43 | 4-methoxy-phenyl | |
| 44 | 2-ethoxy-phenyl | |
| 45 | 3-ethoxy-phenyl | |
| 46 | 4-ethoxy-phenyl | |
| 47 | 2-n-propoxy-phenyl | |
| 48 | 3-n-propoxy-phenyl | |
| 49 | 4-n-propoxy-phenyl | |
| 50 | 2-i-propoxy-phenyl | |
| 51 | 3-i-propoxy-phenyl | |
| 52 | 4-i-propoxy-phenyl | |
| 53 | 2-n-butoxy-phenyl | |
| 54 | 3-n-butoxy-phenyl | |
| 55 | 4-n-butoxy-phenyl | |
| 56 | 2-sec.-butoxy-phenyl | |
| 57 | 3-sec.-butoxy-phenyl | |
| 58 | 4-sec.-butoxy-phenyl | |
| 59 | 2-iso-butoxy-phenyl | |
| 60 | 3-iso-butoxy-phenyl | |
| 61 | 4-iso-butoxy-phenyl | |
| 62 | 2-tert.-butoxyphenyl | |
| 63 | 3-tert.-butoxyphenyl | |
| 64 | 4-tert.-butoxyphenyl | |
| 65 | 2-ethyl-phenyl | |
| 66 | 3-ethyl-phenyl | |
| 67 | 4-ethyl-phenyl | |
| 68 | 2-n-propyl-phenyl | |
| 69 | 3-n-propyl-phenyl | |
| 70 | 4-n-propyl-phenyl | |
| 71 | 2-i-propyl-phenyl | |
| 72 | 3-i-propyl-phenyl | |
| 73 | 4-i-propyl-phenyl | |
| 74 | 2-n-butylphenyl | |
| 75 | 3-n-butylphenyl | |
| 76 | 4-n-butylphenyl | |
| 77 | 2-iso-butyl-phenyl | |
| 78 | 3-iso-butyl-phenyl | |
| 79 | 4-iso-butyl-phenyl | |
| 80 | 2-sec.-butylphenyl | |
| 81 | 3-sec.-butylphenyl | |
| 82 | 4-sec.-butylphenyl | |
| 83 | 2-tert.-butylphenyl | |
| 84 | 3-tert.-butylphenyl | |
| 85 | 4-tert.-butylphenyl | |
| 86 | 3-NO$_2$-phenyl | |
| 87 | 4-NO$_2$-phenyl | |
| 88 | 2-CF$_3$-phenyl | |
| 89 | 3-CF$_3$-phenyl | |
| 90 | 2-CN-phenyl | |
| 91 | 3-CN-phenyl | |
| 92 | 4-CN-phenyl | |
| 93 | 2-(CH$_2$C≡N)-phenyl | |
| 94 | 3-(CH$_2$C≡N)-phenyl | |
| 95 | 4-(CH$_2$C≡N)-phenyl | |
| 96 | 2-CH$_3$CO-phenyl | |
| 97 | 3-CH$_3$CO-phenyl | |
| 98 | 4-CH$_3$CO-phenyl | |
| 99 | 2-CHO-phenyl | |
| 100 | 3-CHO-phenyl | |
| 101 | 4-CHO-phenyl | |
| 102 | 2-NMe$_2$-phenyl | |
| 103 | 3-NMe$_2$-phenyl | |

TABLE 3-continued

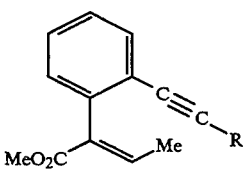

| No. | R | phys. data (m.p. [°C.]); IR [cm$^{-1}$]; $^1$H-NMR [δ scale] |
|---|---|---|
| 104 | 4-NMe$_2$-phenyl | |
| 105 | 2-CO$_2$Me-phenyl | |
| 106 | 3-CO$_2$Me-phenyl | |
| 107 | 4-CO$_2$Me-phenyl | |
| 108 | 2-CO$_2$Et-phenyl | |
| 109 | 3-CO$_2$Et-phenyl | |
| 110 | 4-CO$_2$Et-phenyl | |
| 111 | 2-OCF$_3$-phenyl | |
| 112 | 3-OCF$_3$-phenyl | |
| 113 | 4-OCF$_3$-phenyl | |
| 114 | 2-phenyl-phenyl | |
| 115 | 3-phenyl-phenyl | |
| 116 | 4-phenyl-phenyl | |
| 117 | 2-phenoxy-phenyl | |
| 118 | 3-phenoxy-phenyl | |
| 119 | 4-phenoxy-phenyl | |
| 120 | 3,4-OCH$_2$O-phenyl | |
| 121 | 3,4-OCH$_2$CH$_2$-phenyl | |
| 122 | 3,4,5-(OCH$_3$)$_3$-phenyl | |
| 123 | 3,4-(OCH$_3$)$_2$-phenyl | |
| 124 | 2,3-Me$_2$-phenyl | |
| 125 | 2,4-Me$_2$-phenyl | |
| 126 | 2,5-Me$_2$-phenyl | |
| 127 | 2,6-Me$_2$-phenyl | |
| 128 | 3,4-Me$_2$-phenyl | |
| 129 | 3,5-Me$_2$-phenyl | |
| 130 | 2,4,6-Me$_3$-phenyl | |
| 131 | 2,3-Cl$_2$-phenyl | |
| 132 | 2,4-Cl$_2$-phenyl | |
| 133 | 2,5-Cl$_2$-phenyl | |
| 134 | 2,6-Cl$_2$-phenyl | |
| 135 | 3,4-Cl$_2$-phenyl | |
| 136 | 3,5-Cl$_2$-phenyl | |
| 137 | 2-methyl, 5-NO$_2$-phenyl | |
| 138 | 2-methyl, 3-NO$_2$-phenyl | |
| 139 | 2-methyl, 4-F-phenyl | |
| 140 | 4-methyl, 3-F-phenyl | |
| 141 | 2,6-Cl$_2$, 4-NO$_2$-phenyl | |
| 142 | 2-NO$_2$, 4-Cl-phenyl | |
| 143 | 2-Cl, 5-CF$_3$-phenyl | |
| 144 | 4-Cl, 3-CF$_3$-phenyl | |
| 145 | 2-methyl, 4-CH$_3$CO-phenyl | |
| 146 | 2-methyl, 5-CH$_3$CO-phenyl | |
| 147 | 2,5-Me$_2$, 4-CH$_3$CO-phenyl | |
| 148 | 2-Me, 4-methoximinomethyl-phenyl | |
| 149 | 2-Me, 5-methoximinomethyl-phenyl | |
| 150 | 2,5-Me$_2$, 4-methoximinomethyl-phenyl | |
| 151 | 2-Me, 4-ethoximinomethyl-phenyl | |
| 152 | 2-Me, 4-n-propoximinomethyl-phenyl | |
| 153 | 2-Me, 4-i-propoximinomethyl-phenyl | |
| 154 | 2-Me, 4-n-butoximinomethyl-phenyl | |
| 155 | 2-Me, 5-ethoximinomethyl-phenyl | |
| 156 | 2,5-Me$_2$, 4-ethoximinomethyl-phenyl | |
| 157 | 1-Me-2-naphthyl | |
| 158 | 1-naphthyl | |
| 159 | 2-naphthyl | |
| 160 | 6-methoxy-2-naphthyl | |
| 161 | 3-(5-phenyl-1,3,4-oxadiazol-2-yl)-phenyl | |
| 162 | 3-(5-naphthyl-1,3,4-oxa-diazol-2-yl)-phenyl | |
| 163 | 2-pyridyl | |
| 164 | 3-pyridyl | |
| 165 | 4-pyridyl | |
| 166 | 5-methyl-2-pyridyl | |
| 167 | 6-methyl-2-pyridyl | |
| 168 | quinolin-3-yl | |
| 169 | 2,8(CF$_3$)$_2$-quinolin-4-yl | |
| 170 | isoquinolin-4-yl | |

TABLE 3-continued

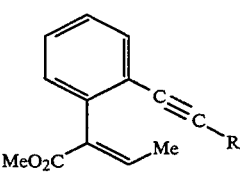

| No. | R | phys. data (m.p. [°C.]); IR [cm$^{-1}$]; $^1$H-NMR [δ scale] |
|---|---|---|
| 171 | thien-2-yl | |
| 172 | thien-3-yl | |
| 173 | 2-chloro-thien-3-yl | |
| 174 | 2-chloro-thien-4-yl | |
| 175 | 3-chloro-thien-2-yl | |
| 176 | 2-chloro-thien-5-yl | |
| 177 | 2,5-Cl$_2$-thien-3-yl | |
| 178 | 3-furyl | |
| 179 | 2-(isoxazol-3-yl)-thien-5-yl | |
| 180 | 2-cyano-thien-3-yl | |
| 181 | 3-Me-thien-2-yl | |
| 182 | 2-NO$_2$-thien-5-yl | |
| 183 | 3-benzothienyl | |
| 184 | 3,5-Me$_2$-isoxazol-3-yl | |
| 185 | 2-thiazolyl | |
| 186 | 5-NO$_2$-thiazol-2-yl | |
| 187 | 5-NO$_2$-imidazol-4-yl | |
| 188 | 4-pyrrazolyl | |
| 189 | 3,5-Me$_2$-pyrrazol-4-yl | |
| 190 | 5-NO$_2$-imidazol-4-yl | |
| 191 | 3-(4-Cl-phenyl)-isoxazol-5-yl | |
| 192 | 4-chloro-3-(3-chlorophenyl)-isoxazol-5-yl | |
| 193 | 5-(4-methylphenyl)-1,3,4-oxadiazol-2-yl | |
| 194 | 5-phenyl-1,3,4-thiadiazol-2-yl | |
| 195 | 3-(4-chlorophenyl)-1,2,4-oxadiazol-5-yl | |
| 196 | 3-isopropyl-isoxazol-5-yl | |
| 197 | 5-(4-F-phenyl)-isoxazol-3-yl | |
| 198 | 4-ethyl-5-phenyl-isoxazol-3-yl | |
| 199 | 4-chloro-5-(3-Cl-phenyl)-isooxazol-3-yl | |
| 200 | CH$_2$Br | |
| 201 | CH$_2$Cl | |
| 202 | CH$_2$I | |

TABLE 4

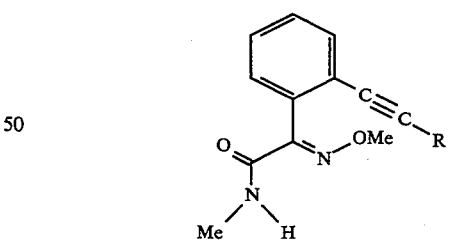

| No. | R | phys. data (m.p. [°C.]); IR [cm$^{-1}$]; $^1$H-NMR [δ scale] |
|---|---|---|
| 1 | H | 2.99; 3.98 (Me); 3.13 (H); 6.80 (NH); 7.21–7.58 (aryl) |
| 2 | SiMe$_3$ | |
| 3 | SnMe$_3$ | |
| 4 | I | |
| 5 | CN | |
| 6 | CH$_2$CH$_3$ | |
| 7 | n-C$_3$H$_7$ | |
| 8 | i-C$_3$H$_7$ | |
| 9 | n-C$_4$H$_9$ | |

TABLE 4-continued

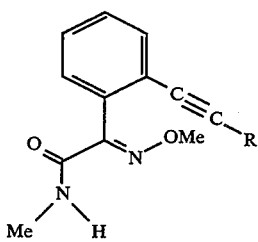

| No. | R | phys. data (m.p. [°C.]); IR [cm$^{-1}$]; $^1$H-NMR [δ scale] |
|---|---|---|
| 10 | i-C$_4$H$_9$ | |
| 11 | s-C$_4$H$_9$ | |
| 12 | t-C$_4$H$_9$ | |
| 13 | n-C$_5$H$_{11}$ | |
| 14 | n-C$_6$H$_{13}$ | |
| 15 | n-C$_7$H$_{15}$ | |
| 16 | n-C$_8$H$_{17}$ | |
| 17 | n-C$_9$H$_{19}$ | |
| 18 | n-C$_{10}$H$_{21}$ | |
| 19 | cyclopropyl | |
| 20 | 1-methyl-cycloprop-1-yl | |
| 21 | cyclobutyl | |
| 22 | cyclopentyl | |
| 23 | cyclohexyl | |
| 24 | cyclohex-1-en-1-yl | |
| 25 | methoxymethyl | |
| 26 | ethoxymethyl | |
| 27 | phenoxymethyl | |
| 28 | benzyloxymethyl | |
| 29 | phenylmethyl | |
| 30 | morpholino-N-methyl | |
| 31 | phenylthiomethyl | |
| 32 | 2-methyl-phenyl | 128–129° C. |
| 33 | 3-methyl-phenyl | |
| 34 | 4-methyl-phenyl | |
| 35 | 2-chloro-phenyl | |
| 36 | 3-chloro-phenyl | |
| 37 | 4-chloro-phenyl | |
| 38 | 2-bromo-phenyl | |
| 39 | 3-bromo-phenyl | |
| 40 | 3-bromo-phenyl | |
| 41 | 2-fluorophenyl | |
| 42 | 3-fluorophenyl | |
| 43 | 4-fluorophenyl | |
| 44 | 2-iodo-phenyl | |
| 45 | 3-iodo-phenyl | |
| 46 | 4-iodo-phenyl | |
| 47 | 2-methoxy-phenyl | |
| 48 | 3-methoxy-phenyl | |
| 49 | 4-methoxy-phenyl | |
| 50 | 2-ethoxy-phenyl | |
| 51 | 3-ethoxy-phenyl | |
| 52 | 4-ethoxy-phenyl | |
| 53 | 2-n-propoxy-phenyl | |
| 54 | 3-n-propoxy-phenyl | |
| 55 | 4-n-propoxy-phenyl | |
| 56 | 2-i-propoxy-phenyl | |
| 57 | 3-i-propoxy-phenyl | |
| 58 | 4-i-propoxy-phenyl | |
| 59 | 2-n-butoxy-phenyl | |
| 60 | 3-n-butoxy-phenyl | |
| 61 | 4-n-butoxy-phenyl | |
| 62 | 2-sec.-butoxy-phenyl | |
| 63 | 3-sec.-butoxy-phenyl | |
| 64 | 4-sec.-butoxy-phenyl | |
| 65 | 2-iso-butoxy-phenyl | |
| 66 | 3-iso-butoxy-phenyl | |
| 67 | 4-iso-butoxy-phenyl | |
| 68 | 2-tert.-butoxyphenyl | |
| 69 | 3-tert.-butoxyphenyl | |
| 70 | 4-tert.-butoxyphenyl | |
| 71 | 2-ethyl-phenyl | |
| 72 | 3-ethyl-phenyl | |
| 73 | 4-ethyl-phenyl | |
| 74 | 2-n-propyl-phenyl | |

TABLE 4-continued

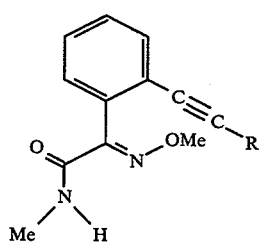

| No. | R | phys. data (m.p. [°C.]); IR [cm$^{-1}$]; $^1$H-NMR [δ scale] |
|---|---|---|
| 75 | 3-n-propyl-phenyl | |
| 76 | 4-n-propyl-phenyl | |
| 77 | 2-i-propyl-phenyl | |
| 78 | 3-i-propyl-phenyl | |
| 79 | 4-i-propyl-phenyl | |
| 80 | 2-n-butylphenyl | |
| 81 | 3-n-butylphenyl | |
| 82 | 4-n-butylphenyl | |
| 83 | 2-iso-butyl-phenyl | |
| 84 | 3-iso-butyl-phenyl | |
| 85 | 4-iso-butyl-phenyl | |
| 86 | 2-sec.-butylphenyl | |
| 87 | 3-sec.-butylphenyl | |
| 88 | 4-sec.-butylphenyl | |
| 89 | 2-tert.-butylphenyl | |
| 90 | 3-tert.-butylphenyl | |
| 91 | 4-tert.-butylphenyl | |
| 92 | 2-NO$_2$-phenyl | |
| 93 | 3-NO$_2$-phenyl | |
| 94 | 4-NO$_2$-phenyl | |
| 95 | 2-CF$_3$-phenyl | |
| 96 | 3-CF$_3$-phenyl | 139–144° C. |
| 97 | 4-CF$_3$-phenyl | |
| 98 | 2-CN-phenyl | |
| 99 | 3-CN-phenyl | |
| 100 | 4-CN-phenyl | |
| 101 | 2-(CH$_2$C≡N)-phenyl | 147–151° C. |
| 102 | 3-(CH$_2$C≡N)-phenyl | |
| 103 | 4-(CH$_2$C≡N)-phenyl | |
| 104 | 2-CH$_3$CO-phenyl | |
| 105 | 3-CH$_3$CO-phenyl | |
| 106 | 4-CH$_3$CO-phenyl | |
| 107 | 2-CHO-phenyl | |
| 108 | 3-CHO-phenyl | |
| 109 | 4-CHO-phenyl | |
| 110 | 2-NMe$_2$-phenyl | |
| 111 | 3-NMe$_2$-phenyl | |
| 112 | 4-NMe$_2$-phenyl | |
| 113 | 2-CO$_2$Me-phenyl | |
| 114 | 3-CO$_2$Me-phenyl | |
| 115 | 4-CO$_2$Me-phenyl | |
| 116 | 2-CO$_2$Et-phenyl | |
| 117 | 3-CO$_2$Et-phenyl | |
| 118 | 4-CO$_2$Et-phenyl | |
| 119 | 2-OCF$_3$-phenyl | |
| 120 | 3-OCF$_3$-phenyl | |
| 121 | 4-OCF$_3$-phenyl | |
| 122 | 2-phenyl-phenyl | |
| 123 | 3-phenyl-phenyl | |
| 124 | 4-phenyl-phenyl | |
| 125 | 2-phenoxy-phenyl | |
| 126 | 3-phenoxy-phenyl | |
| 127 | 4-phenoxy-phenyl | |
| 128 | 3,4-OCH$_2$O-phenyl | |
| 129 | 3,4-OCH$_2$CH$_2$-phenyl | |
| 130 | 3,4,5-(OCH$_3$)$_3$-phenyl | |
| 131 | 3,4-(OCH$_3$)$_2$-phenyl | |
| 132 | 2,3-Me$_2$-phenyl | |
| 133 | 2,4-Me$_2$-phenyl | |
| 134 | 2,5-Me$_2$-phenyl | |
| 135 | 2,6-Me$_2$-phenyl | |
| 136 | 3,4-Me$_2$-phenyl | |
| 137 | 3,5-Me$_2$-phenyl | |
| 138 | 2,4,6-Me$_3$-phenyl | |
| 139 | 2,3-Cl$_2$-phenyl | 130–132° C. |

TABLE 4-continued

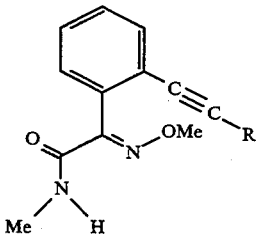

| No. | R | phys. data (m.p. [°C.]); IR [cm$^{-1}$]; $^1$H-NMR [δ scale] |
|---|---|---|
| 140 | 2,4-Cl$_2$-phenyl | 143–145° C. |
| 141 | 2,5-Cl$_2$-phenyl | 134–137° C. |
| 142 | 2,6-Cl$_2$-phenyl | |
| 143 | 3,4-Cl$_2$-phenyl | 147–150° C. |
| 144 | 3,5-Cl$_2$-phenyl | 159–163° C. |
| 145 | 2-methyl, 5-NO$_2$-phenyl | |
| 146 | 2-methyl, 3-NO$_2$-phenyl | |
| 147 | 2-methyl, 4-F-phenyl | |
| 148 | 4-methyl, 3-F-phenyl | |
| 149 | 2,6-Cl$_2$, 4-NO$_2$-phenyl | |
| 150 | 2-NO$_2$, 4-Cl-phenyl | 192° C. |
| 151 | 2-Cl, 5-CF$_3$-phenyl | |
| 152 | 4-Cl, 3-CF$_3$-phenyl | |
| 153 | 2-methyl, 4-CH$_3$CO-phenyl | |
| 154 | 2-methyl, 5-CH$_3$CO-phenyl | |
| 155 | 2,5-Me$_2$, 4-CH$_3$CO-phenyl | |
| 156 | 2-Me, 4-methoximinomethyl-phenyl | 136–140° C. |
| 157 | 2-Me, 5-methoximinomethyl-phenyl | 2,12; 2,45; 2,93; 3,96; 3,99 (Me); 6,79 (NH); 7,18–7,71 (Aryl) |
| 158 | 2,5-Me$_2$, 4-methoximinomethyl-phenyl | |
| 159 | 2-Me, 4-ethoximinomethyl-phenyl | |
| 160 | 2-Me, 4-n-propoximinomethyl-phenyl | |
| 161 | 2-Me, 4-i-propoximinomethyl-phenyl | |
| 162 | 2-Me, 4-n-butoximinomethyl-phenyl | |
| 163 | 2-Me, 5-ethoximinomethyl-phenyl | |
| 164 | 2,5-Me$_2$, 4-ethoximinomethylphenyl | |
| 165 | 3-(5-phenyl-1,3,4-oxadiazol-2-yl)-phenyl | |
| 166 | 3-(5-naphthyl-1,3,4-oxadiazol-2-yl)-phenyl | |
| 167 | 2-pyridyl | |
| 168 | 3-pyridyl | |
| 169 | 4-pyridyl | |
| 170 | 5-methyl-2-pyridyl | |
| 171 | 6-methyl-2-pyridyl | |
| 172 | quinolin-3-yl | |
| 173 | 2,8(CF$_3$)$_2$-quinolin-4-yl | |
| 174 | isoquinolin-4-yl | |
| 175 | thien-2-yl | |
| 176 | thien-3-yl | |
| 177 | 2-chloro-thien-3-yl | |
| 178 | 2-chloro-thien-4-yl | |
| 179 | 3-chloro-thien-2-yl | |
| 180 | 2-chloro-thien-5-yl | |
| 181 | 2,5-Cl$_2$-thien-3-yl | |
| 182 | 3-furyl | |
| 183 | 2-(isoxazol-3-yl)-thien-5-yl | |
| 184 | 2-cyano-thien-3-yl | |
| 185 | 3-Me-thien-2-yl | |
| 186 | 2-NO$_2$-thien-5-yl | |
| 187 | 3-benzothienyl | |
| 188 | 3,5-Me$_2$-isoxazol-3-yl | |
| 189 | 2-Thiazolyl | |
| 190 | 5-NO$_2$-thiazol-2-yl | |
| 191 | 5-NO$_2$-imidazol-4-yl | |
| 192 | 4-pyrrazolyl | |
| 193 | 3,5-Me$_2$-pyrrazol-4-yl | |
| 194 | 3-(4-Cl-phenyl)-isoxazol-5-yl | |
| 195 | 4-chloro-3-(3-chlorophenyl)-isoxazol-5-yl | |
| 196 | 5-(4-methylphenyl)-1,3,4-oxadiazol-2-yl | |
| 197 | 5-phenyl-1,3,4-thiadiazol-2-yl | |
| 198 | 3-(4-chlorophenyl)-1,2,4-oxadiazol-5-yl | |
| 199 | 3-isopropyl-isoxazol-5-yl | |
| 200 | 5-(4-F-phenyl)-isoxazol-3-yl | |
| 201 | 4-ethyl-5-phenyl-isoxazol-3-yl | |
| 202 | 4-chloro-5-(3-Cl-phenyl)-isoxazol-3-yl | |
| 203 | CH$_2$Br | |
| 204 | CH$_2$Cl | |
| 205 | CH$_2$I | |
| 206 | 1-naphthyl | |
| 207 | 2-naphthyl | 155–158° C. |
| 208 | 6-methoxy-naphth-2-yl | |
| 209 | CH=CH-phenyl | 109–112° C. |

TABLE 5

R' = R$^1$ or R$^{18}$

| No. | R$^{18}$ | phys. data m.p. [°C.] IR [cm$^{-1}$] $^1$H-NMR [δ scale] |
|---|---|---|
| 1 | OH | |
| 2 | O-methyl | |
| 3 | O-ethyl | |
| 4 | O-(n-propyl) | |
| 5 | O-(i-propyl) | |
| 6 | O-(n-butyl) | |
| 7 | O-(i-butyl) | |
| 8 | O-(s-butyl) | |
| 9 | O-(tert.-butyl) | |
| 10 | O-benzyl | |
| 11 | O-(2-methylbenzyl) | |
| 12 | O-(3-methylbenzyl) | |
| 13 | O-(4-methylbenzyl) | |
| 14 | O-(2-Cl-benzyl) | |
| 15 | O-(3-Cl-benzyl) | |
| 16 | O-(4-Cl-benzyl) | |
| 17 | methyl | |
| 18 | ethyl | |
| 19 | n-propyl | |
| 20 | i-propyl | |
| 21 | n-butyl | |
| 22 | i-butyl | |
| 23 | s-butyl | |
| 24 | tert.-butyl | |
| 25 | benzyl | |
| 26 | phenyl | |
| 27 | 2-Me-phenyl | |
| 28 | 3-Me-phenyl | |
| 29 | 4-Me-phenyl | |
| 30 | 2-F-phenyl | |
| 31 | 3-F-phenyl | |
| 32 | 4-F-phenyl | |

TABLE 5-continued

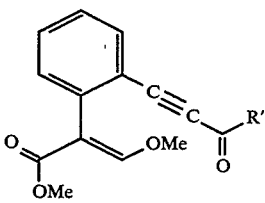

R' = R¹ or R¹⁸

| No. | R¹⁸ | phys. data m.p. [°C.] IR [cm⁻¹] ¹H-NMR [δ scale] |
|---|---|---|
| 33 | 2-Cl-phenyl | |
| 34 | 3-Cl-phenyl | |
| 35 | 4-Cl-phenyl | |
| 36 | 2-Br-phenyl | |
| 37 | 3-Br-phenyl | |
| 38 | 4-Br-phenyl | |
| 39 | 2-I-phenyl | |
| 40 | 3-I-phenyl | |
| 41 | 4-I-phenyl | |
| 42 | 2-CF₃-phenyl | |
| 43 | 3-CF₃-phenyl | |
| 44 | 4-CF₃-phenyl | |
| 45 | 2-OCH₃-phenyl | |
| 46 | 3-OCH₃-phenyl | |
| 47 | 4-OCH₃-phenyl | |
| 48 | 2-CN-phenyl | |
| 49 | 3-CN-phenyl | |
| 50 | 4-CN-phenyl | |
| 51 | 2-NO₂-phenyl | |
| 52 | 3-NO₂-phenyl | |
| 53 | 4-NO₂-phenyl | |
| 54 | 2-OCF₃-phenyl | |
| 55 | 3-OCF₃-phenyl | |
| 56 | 4-OCF₃-phenyl | |
| 57 | 2-CCl₃-phenyl | |
| 58 | 3-CCl₃-phenyl | |
| 59 | 4-CCl₃-phenyl | |
| 60 | 2-NMe₂-phenyl | |
| 61 | 3-NMe₂-phenyl | |
| 62 | 4-NMe₂-phenyl | |
| 63 | 2-tert.-butylphenyl | |
| 64 | 3-tert.-butylphenyl | |
| 65 | 4-tert.-butylphenyl | |
| 66 | 2-tert.-butoxyphenyl | |
| 67 | 3-tert.-butoxyphenyl | |
| 68 | 4-tert.-butoxyphenyl | |
| 69 | 2-phenylphenyl | |
| 70 | 3-phenylphenyl | |
| 71 | 4-phenylphenyl | |
| 72 | 2-phenoxyphenyl | |
| 73 | 3-phenoxyphenyl | |
| 74 | 4-phenoxyphenyl | |
| 75 | 1-naphthyl | |
| 76 | 2-naphthyl | |
| 77 | 2,3-Me₂-phenyl | |
| 78 | 2,4-Me₂-phenyl | |
| 79 | 2,5-Me₂-phenyl | |
| 80 | 2,6-Me₂-phenyl | |
| 81 | 3,4-Me₂-phenyl | |
| 82 | 3,5-Me₂-phenyl | |
| 83 | 2,4,6-Me₃-phenyl | |
| 84 | 2,3-Cl₂-phenyl | |
| 85 | 2,4-Cl₂-phenyl | |
| 86 | 2,5-Cl₂-phenyl | |
| 87 | 2,6-Cl₂-phenyl | |
| 88 | 3,4-Cl₂-phenyl | |
| 89 | 3,5-Cl₂-phenyl | |
| 90 | 2-pyridyl | |
| 91 | 3-pyridyl | |
| 92 | 4-pyridyl | |
| 93 | 2-furyl | |
| 94 | 3-furyl | |
| 95 | 2-(5-NO₂-furyl) | |
| 96 | 2-thienyl | |
| 97 | 2-(5-Cl-thienyl) | |
| 98 | 2-(3-Cl-thienyl) | |
| 99 | 3-(thienyl) | |

TABLE 5-continued

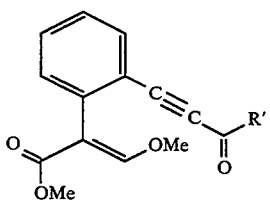

R' = R¹ or R¹⁸

| No. | R¹⁸ | phys. data m.p. [°C.] IR [cm⁻¹] ¹H-NMR [δ scale] |
|---|---|---|
| 100 | 2-benzofuranyl | |
| 101 | 2-benzothienyl | |
| 102 | 5-isoxazolyl | |
| 103 | 3-(2-Cl-pyridyl) | |
| 104 | 3-(6-Cl-pyridyl) | |
| 105 | 4-(2,6-Cl₂-pyridyl) | |
| 106 | 3-(5,6-Cl₂-pyridyl) | |
| 107 | 3-(2-phenoxypyridyl) | |

TABLE 6

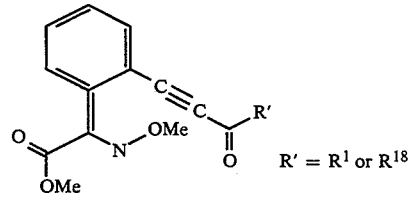

R' = R¹ or R¹⁸

| No. | R¹⁸ | phys. data m.p. [°C.] IR [cm⁻¹] ¹H-NMR [δ scale] |
|---|---|---|
| 1 | OH | |
| 2 | O-methyl | |
| 3 | O-ethyl | |
| 4 | O-(n-propyl) | |
| 5 | O-(i-propyl) | |
| 6 | O-(n-butyl) | |
| 7 | O-(i-butyl) | |
| 8 | O-(s-butyl) | |
| 9 | O-(tert.-butyl) | |
| 10 | O-benzyl | |
| 11 | O-(2-methylbenzyl) | |
| 12 | O-(3-methylbenzyl) | |
| 13 | O-(4-methylbenzyl) | |
| 14 | O-(2-Cl-benzyl) | |
| 15 | O-(3-Cl-benzyl) | |
| 16 | O-(4-Cl-benzyl) | |
| 17 | methyl | |
| 18 | ethyl | |
| 19 | n-propyl | |
| 20 | i-propyl | |
| 21 | n-butyl | |
| 22 | i-butyl | |
| 23 | s-butyl | |
| 24 | tert.-butyl | |
| 25 | benzyl | |
| 26 | phenyl | 89–94° C. |
| 27 | 2-Me-phenyl | 95–98° C. |
| 28 | 3-Me-phenyl | 90–92° C. |
| 29 | 4-Me-phenyl | 103–112° C. |
| 30 | 2-F-phenyl | |
| 31 | 3-F-phenyl | |
| 32 | 4-F-phenyl | |
| 33 | 2-Cl-phenyl | 88–93° C. |
| 34 | 3-Cl-phenyl | 97–102° C. |
| 35 | 4-Cl-phenyl | 3.87, 4.07 (OCH₃), 7.35–8.11 ppm (8H). |
| 36 | 2-Br-phenyl | |
| 37 | 3-Br-phenyl | |
| 38 | 4-Br-phenyl | 98–104° C. |
| 39 | 2-I-phenyl | |

TABLE 6-continued

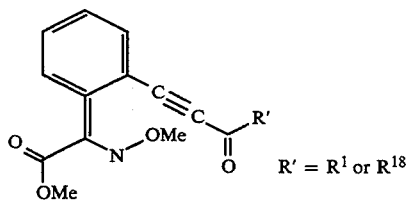

R' = R¹ or R¹⁸

| No. | R¹⁸ | phys. data m.p. [°C.] IR [cm⁻¹] ¹H-NMR [δ scale] |
|---|---|---|
| 40 | 3-I-phenyl | |
| 41 | 4-I-phenyl | |
| 42 | 2-CF₃-phenyl | 2.82, 4.03 (OCH₃), 7.34–8.11 ppm (8H). |
| 43 | 3-CF₃-phenyl | 88–90° C. |
| 44 | 4-CF₃-phenyl | 3.87, 4.07 (OCH₃), 7.35–8.28 ppm (8H). |
| 45 | 2-OCH₃-phenyl | |
| 46 | 3-OCH₃-phenyl | |
| 47 | 4-OCH₃-phenyl | |
| 48 | 2-CN-phenyl | |
| 49 | 3-CN-phenyl | |
| 50 | 4-CN-phenyl | |
| 51 | 2-NO₂-phenyl | |
| 52 | 3-NO₂-phenyl | |
| 53 | 4-NO₂-phenyl | |
| 54 | 2-OCF₃-phenyl | |
| 55 | 3-OCF₃-phenyl | |
| 56 | 4-OCF₃-phenyl | |
| 57 | 2-CCl₃-phenyl | |
| 58 | 3-CCl₃-phenyl | |
| 59 | 4-CCl₃-phenyl | |
| 60 | 2-NMe₂-phenyl | |
| 61 | 3-NMe₂-phenyl | |
| 62 | 4-NMe₂-phenyl | |
| 63 | 2-tert.-butylphenyl | |
| 64 | 3-tert.-butylphenyl | |
| 65 | 4-tert.-butylphenyl | |
| 66 | 2-tert.-butoxyphenyl | |
| 67 | 3-tert.-butoxyphenyl | |
| 68 | 4-tert.-butoxyphenyl | |
| 69 | 2-phenylphenyl | |
| 70 | 3-phenylphenyl | |
| 71 | 4-phenylphenyl | |
| 72 | 2-phenoxyphenyl | |
| 73 | 3-phenoxyphenyl | |
| 74 | 4-phenoxyphenyl | |
| 75 | 1-naphthyl | |
| 76 | 2-naphthyl | |
| 77 | 2,3-Me₂-phenyl | |
| 78 | 2,4-Me₂-phenyl | |
| 79 | 2,5-Me₂-phenyl | |
| 80 | 2,6-Me₂-phenyl | |
| 81 | 3,4-Me₂-phenyl | |
| 82 | 3,5-Me₂-phenyl | |
| 83 | 2,4,6-Me₃-phenyl | |
| 84 | 2,3-Cl₂-phenyl | |
| 85 | 2,4-Cl₂-phenyl | 107–112° C. |
| 86 | 2,5-Cl₂-phenyl | |
| 87 | 2,6-Cl₂-phenyl | |
| 88 | 3,4-Cl₂-phenyl | |
| 89 | 3,5-Cl₂-phenyl | 152–157° C. |
| 90 | 2-pyridyl | |
| 91 | 3-pyridyl | |
| 92 | 4-pyridyl | |
| 93 | 2-furyl | |
| 94 | 3-furyl | |
| 95 | 2-(5-NO₂-furyl) | |
| 96 | 2-thienyl | |
| 97 | 2-(5-Cl-thienyl) | |
| 98 | 2-(3-Cl-thienyl) | |
| 99 | 3-(thienyl) | |
| 100 | 2-benzofuranyl | |
| 101 | 2-benzothienyl | |
| 102 | 5-isoxazolyl | |
| 103 | 3-(2-Cl-pyridyl) | |
| 104 | 3-(6-Cl-pyridyl) | |

TABLE 6-continued

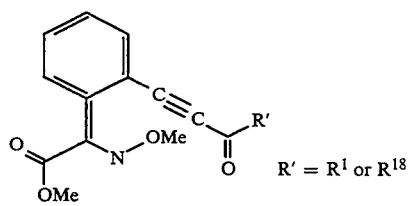

R' = R¹ or R¹⁸

| No. | R¹⁸ | phys. data m.p. [°C.] IR [cm⁻¹] ¹H-NMR [δ scale] |
|---|---|---|
| 105 | 4-(2,6-Cl₂-pyridyl) | |
| 106 | 3-(5,6-Cl₂-pyridyl) | |
| 107 | 3-(2-phenoxypyridyl) | |

TABLE 7

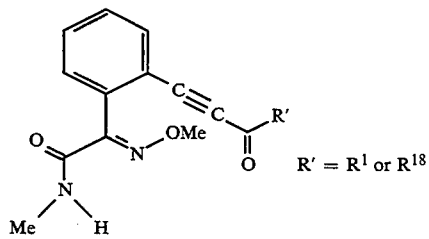

R' = R¹ or R¹⁸

| No. | R¹⁸ | phys. data m.p. [°C.] IR [cm⁻¹] ¹H-NMR [δ scale] |
|---|---|---|
| 1 | OH | |
| 2 | O-methyl | |
| 3 | O-ethyl | |
| 4 | O-(n-propyl) | |
| 5 | O-(i-propyl) | |
| 6 | O-(n-butyl) | |
| 7 | O-(i-butyl) | |
| 8 | O-(s-butyl) | |
| 9 | O-(tert.-butyl) | |
| 10 | O-benzyl | |
| 11 | O-(2-methylbenzyl) | |
| 12 | O-(3-methylbenzyl) | |
| 13 | O-(4-methylbenzyl) | |
| 14 | O-(2-Cl-benzyl) | |
| 15 | O-(3-Cl-benzyl) | |
| 16 | O-(4-Cl-benzyl) | |
| 17 | methyl | |
| 18 | ethyl | |
| 19 | n-propyl | |
| 20 | i-propyl | |
| 21 | n-butyl | |
| 22 | i-butyl | |
| 23 | s-butyl | |
| 24 | tert.-butyl | |
| 25 | benzyl | |
| 26 | phenyl | |
| 27 | 2-Me-phenyl | |
| 28 | 3-Me-phenyl | |
| 29 | 4-Me-phenyl | |
| 30 | 2-F-phenyl | |
| 31 | 3-F-phenyl | |
| 32 | 4-F-phenyl | |
| 33 | 2-Cl-phenyl | |
| 34 | 3-Cl-phenyl | |
| 35 | 4-Cl-phenyl | |
| 36 | 2-Br-phenyl | |
| 37 | 3-Br-phenyl | |
| 38 | 4-Br-phenyl | |
| 39 | 2-I-phenyl | |
| 40 | 3-I-phenyl | |
| 41 | 4-I-phenyl | |
| 42 | 2-CF₃-phenyl | |
| 43 | 3-CF₃-phenyl | |

TABLE 7-continued

Structure: phenyl ring with C≡C-C(=O)-R' substituent and C(=N-OMe) group attached to C(=O)-N(Me)H; R' = R¹ or R¹⁸ phys. data
m.p. [°C.]
IR [cm⁻¹]
¹H-NMR [δ scale]

| No. | R¹⁸ |
|---|---|
| 44 | 4-CF₃-phenyl |
| 45 | 2-OCH₃-phenyl |
| 46 | 3-OCH₃-phenyl |
| 47 | 4-OCH₃-phenyl |
| 48 | 2-CN-phenyl |
| 49 | 3-CN-phenyl |
| 50 | 4-CN-phenyl |
| 51 | 2-NO₂-phenyl |
| 52 | 3-NO₂-phenyl |
| 53 | 4-NO₂-phenyl |
| 54 | 2-OCF₃-phenyl |
| 55 | 3-OCF₃-phenyl |
| 56 | 4-OCF₃-phenyl |
| 57 | 2-CCl₃-phenyl |
| 58 | 3-CCl₃-phenyl |
| 59 | 4-CCl₃-phenyl |
| 60 | 2-NMe₂-phenyl |
| 61 | 3-NMe₂-phenyl |
| 62 | 4-NMe₂-phenyl |
| 63 | 2-tert.-butylphenyl |
| 64 | 3-tert.-butylphenyl |
| 65 | 4-tert.-butylphenyl |
| 66 | 2-tert.-butoxyphenyl |
| 67 | 3-tert.-butoxyphenyl |
| 68 | 4-tert.-butoxyphenyl |
| 69 | 2-phenylphenyl |
| 70 | 3-phenylphenyl |
| 71 | 4-phenylphenyl |
| 72 | 2-phenoxyphenyl |
| 73 | 3-phenoxyphenyl |
| 74 | 4-phenoxyphenyl |
| 75 | 1-naphthyl |
| 76 | 2-naphthyl |
| 77 | 2,3-Me₂-phenyl |
| 78 | 2,4-Me₂-phenyl |
| 79 | 2,5-Me₂-phenyl |
| 80 | 2,6-Me₂-phenyl |
| 81 | 3,4-Me₂-phenyl |
| 82 | 3,5-Me₂-phenyl |
| 83 | 2,4,6-Me₃-phenyl |
| 84 | 2,3-Cl₂-phenyl |
| 85 | 2,4-Cl₂-phenyl |
| 86 | 2,5-Cl₂-phenyl |
| 87 | 2,6-Cl₂-phenyl |
| 88 | 3,4-Cl₂-phenyl |
| 89 | 3,5-Cl₂-phenyl |
| 90 | 2-pyridyl |
| 91 | 3-pyridyl |
| 92 | 4-pyridyl |
| 93 | 2-furyl |
| 94 | 3-furyl |
| 95 | 2-(5-NO₂-furyl) |
| 96 | 2-thienyl |
| 97 | 2-(5-Cl-thienyl) |
| 98 | 2-(3-Cl-thienyl) |
| 99 | 3-(thienyl) |
| 100 | 2-benzofuranyl |
| 101 | 2-benzothienyl |
| 102 | 5-isoxazolyl |
| 103 | 3-(2-Cl-pyridyl) |
| 104 | 3-(6-Cl-pyridyl) |
| 105 | 4-(2,6-Cl₂-pyridyl) |
| 106 | 3-(5,6-Cl₂-pyridyl) |
| 107 | 3-(2-phenoxypyridyl) |

TABLE 8

Structure: phenyl ring with C≡C-C(=O)-R' substituent and C(=CH-Me)-C(=O)-OMe group; R' = R¹ or R¹⁸ phys. data
m.p. [°C.]
IR [cm⁻¹]
¹H-NMR [δ scale]

| No. | R¹⁸ |
|---|---|
| 1 | OH |
| 2 | O-methyl |
| 3 | O-ethyl |
| 4 | O-(n-propyl) |
| 5 | O-(i-propyl) |
| 6 | O-(n-butyl) |
| 7 | O-(i-butyl) |
| 8 | O-(s-butyl) |
| 9 | O-(tert.-butyl) |
| 10 | O-benzyl |
| 11 | O-(2-methylbenzyl) |
| 12 | O-(3-methylbenzyl) |
| 13 | O-(4-methylbenzyl) |
| 14 | O-(2-Cl-benzyl) |
| 15 | O-(3-Cl-benzyl) |
| 16 | O-(4-Cl-benzyl) |
| 17 | methyl |
| 18 | ethyl |
| 19 | n-propyl |
| 20 | i-propyl |
| 21 | n-butyl |
| 22 | i-butyl |
| 23 | s-butyl |
| 24 | tert.-butyl |
| 25 | benzyl |
| 26 | phenyl |
| 27 | 2-Me-phenyl |
| 28 | 3-Me-phenyl |
| 29 | 4-Me-phenyl |
| 30 | 2-F-phenyl |
| 31 | 3-F-phenyl |
| 32 | 4-F-phenyl |
| 33 | 2-Cl-phenyl |
| 34 | 3-Cl-phenyl |
| 35 | 4-Cl-phenyl |
| 36 | 2-Br-phenyl |
| 37 | 3-Br-phenyl |
| 38 | 4-Br-phenyl |
| 39 | 2-I-phenyl |
| 40 | 3-I-phenyl |
| 41 | 4-I-phenyl |
| 42 | 2-CF₃-phenyl |
| 43 | 3-CF₃-phenyl |
| 44 | 4-CF₃-phenyl |
| 45 | 2-OCH₃-phenyl |
| 46 | 3-OCH₃-phenyl |
| 47 | 4-OCH₃-phenyl |
| 48 | 2-CN-phenyl |
| 49 | 3-CN-phenyl |
| 50 | 4-CN-phenyl |
| 51 | 2-NO₂-phenyl |
| 52 | 3-NO₂-phenyl |
| 53 | 4-NO₂-phenyl |
| 54 | 2-OCF₃-phenyl |
| 55 | 3-OCF₃-phenyl |
| 56 | 4-OCF₃-phenyl |
| 57 | 2-CCl₃-phenyl |
| 58 | 3-CCl₃-phenyl |
| 59 | 4-CCl₃-phenyl |
| 60 | 2-NMe₂-phenyl |
| 61 | 3-NMe₂-phenyl |
| 62 | 4-NMe₂-phenyl |
| 63 | 2-tert.-butylphenyl |
| 64 | 3-tert.-butylphenyl |
| 65 | 4-tert.-butylphenyl |
| 66 | 2-tert.-butoxyphenyl |
| 67 | 3-tert.-butoxyphenyl |

TABLE 8-continued

Structure: 2-substituted phenyl with C≡C-C(=CHMe)- and -C(=O)R' where R' = R¹ or R¹⁸, and C(=O)OMe group.

| No. | R¹⁸ | phys. data m.p. [°C.] IR [cm⁻¹] ¹H-NMR [δ scale] |
|---|---|---|
| 68 | 4-tert.-butoxyphenyl | |
| 69 | 2-phenylphenyl | |
| 70 | 3-phenylphenyl | |
| 71 | 4-phenylphenyl | |
| 72 | 2-phenoxyphenyl | |
| 73 | 3-phenoxyphenyl | |
| 74 | 4-phenoxyphenyl | |
| 75 | 1-naphthyl | |
| 76 | 2-naphthyl | |
| 77 | 2,3-Me₂-phenyl | |
| 78 | 2,4-Me₂-phenyl | |
| 79 | 2,5-Me₂-phenyl | |
| 80 | 2,6-Me₂-phenyl | |
| 81 | 3,4-Me₂-phenyl | |
| 82 | 3,5-Me₂-phenyl | |
| 83 | 2,4,6-Me₃-phenyl | |
| 84 | 2,3-Cl₂-phenyl | |
| 85 | 2,4-Cl₂-phenyl | |
| 86 | 2,5-Cl₂-phenyl | |
| 87 | 2,6-Cl₂-phenyl | |
| 88 | 3,4-Cl₂-phenyl | |
| 89 | 3,5-Cl₂-phenyl | |
| 90 | 2-pyridyl | |
| 91 | 3-pyridyl | |
| 92 | 4-pyridyl | |
| 93 | 2-furyl | |
| 94 | 3-furyl | |
| 95 | 2-(5-NO₂-furyl) | |
| 96 | 2-thienyl | |
| 97 | 2-(5-Cl-thienyl) | |
| 98 | 2-(3-Cl-thienyl) | |
| 99 | 3-(thienyl) | |
| 100 | 2-benzofuranyl | |
| 101 | 2-benzothienyl | |
| 102 | 5-isoxazolyl | |
| 103 | 3-(2-Cl-pyridyl) | |
| 104 | 3-(6-Cl-pyridyl) | |
| 105 | 4-(2,6-Cl₂-pyridyl) | |
| 106 | 3-(5,6-Cl₂-pyridyl) | |
| 107 | 3-(2-phenoxypyridyl) | |

TABLE 9

Structure: 2-substituted phenyl with C≡C-C(=NOMe)R²⁰ and C(=NOMe)C(=O)OMe group.

| No. | R²⁰ | phys. data m.p. [°C.] IR [cm⁻¹] ¹H-NMR [δ scale] |
|---|---|---|
| 1 | methyl | |
| 2 | ethyl | |
| 3 | n-propyl | |
| 4 | i-propyl | |
| 5 | n-butyl | |
| 6 | i-butyl | |
| 7 | s-butyl | |
| 8 | tert-butyl | |

TABLE 9-continued

| No. | R²⁰ | phys. data m.p. [°C.] IR [cm⁻¹] ¹H-NMR [δ scale] |
|---|---|---|
| 9 | benzyl | |
| 10 | phenyl | 3.81; 4.04; 4.12 (CH₃); 7.28–7.88 ppm (9H) |
| 11 | 2-Me-phenyl | |
| 12 | 3-Me-phenyl | 2.42; 3.81, 4.05; 4.12 (CH₃); 7.17–7.71 ppm (8H). |
| 13 | 4-Me-phenyl | 2.38; 3.82; 4.05; 4.11 (CH₃); 7.18–7.75 ppm (8H). |
| 14 | 2-F-phenyl | |
| 15 | 3-F-phenyl | |
| 16 | 4-F-phenyl | |
| 17 | 2-Cl-phenyl | 3.76; 4.00; 4.12 (CH₃); 7.28–7.61 ppm (8H). |
| 18 | 3-Cl-phenyl | |
| 19 | 4-Cl-phenyl | |
| 20 | 2-Br-phenyl | |
| 21 | 3-Br-phenyl | |
| 22 | 4-Br-phenyl | |
| 23 | 2-I-phenyl | |
| 24 | 3-I-phenyl | |
| 25 | 4-I-phenyl | |
| 26 | 2-CF₃-phenyl | |
| 27 | 3-CF₃-phenyl | 3.81; 4.05; 4.15 (CH₃); 7.28–8.11 ppm (8H). |
| 28 | 4-CF₃-phenyl | 3.82; 4.05; 4.15 (CH₃); 7.30–7.98 ppm (8H). |
| 29 | 2-OCH₃-phenyl | |
| 30 | 3-OCH₃-phenyl | |
| 31 | 4-OCH₃-phenyl | |
| 32 | 2-CN-pheny | |
| 33 | 3-CN-phenyl | |
| 34 | 4-CN-phenyl | |
| 35 | 2-NO₂-phenyl | |
| 36 | 3-NO₂-phenyl | |
| 37 | 4-NO₂-phenyl | |
| 38 | 2-OCF₃-phenyl | |
| 39 | 3-OCF₃-phenyl | |
| 40 | 4-OCF₃-phenyl | |
| 41 | 2-CCl₃- phenyl | |
| 42 | 3-CCl₃- phenyl | |
| 43 | 4-CCl₃- phenyl | |
| 44 | 2-NMe₂- phenyl | |
| 45 | 3-NMe₂- phenyl | |
| 46 | 4-NMe₂- phenyl | |
| 47 | 2-tert.-butylphenyl | |
| 48 | 3-tert.-butylphenyl | |
| 49 | 4-tert.-butylphenyl | |
| 50 | 2-tert.-butoxyphenyl | |
| 51 | 3-tert.-butoxyphenyl | |
| 52 | 4-tert.-butoxyphenyl | |
| 53 | 2-phenylphenyl | |
| 54 | 3-phenylphenyl | |
| 55 | 4-phenylphenyl | |
| 56 | 2-phenoxyphenyl | |
| 57 | 3-phenoxyphenyl | |
| 58 | 4-phenoxyphenyl | |
| 59 | 1-naphthyl | |
| 60 | 2-naphthyl | |
| 61 | 2,3-Me₂-phenyl | |
| 62 | 2,4-Me₂-phenyl | |
| 63 | 2,5-Me₂-phenyl | |
| 64 | 2,6-Me₂-phenyl | |
| 65 | 3,4-Me₂-phenyl | |
| 66 | 3,5-Me₂-phenyl | |
| 67 | 2,4,6-Me₃-phenyl | |
| 68 | 2,3-Cl₂-phenyl | |
| 69 | 2,4-Cl₂-phenyl | |

TABLE 9-continued

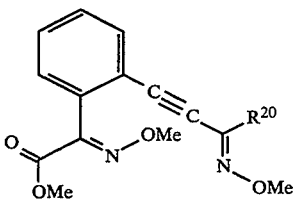

| No. | R20 | phys. data m.p. [°C.] IR [cm−1] 1H-NMR [δ scale] |
|---|---|---|
| 70 | 2,5-Cl2-phenyl | |
| 71 | 2,6-Cl2-phenyl | |
| 72 | 3,4-Cl2-phenyl | |
| 73 | 3,5-Cl2-phenyl | |
| 74 | 2-pyridyl | |
| 75 | 3-pyridyl | |
| 76 | 4-pyridyl | |
| 77 | 2-furyl | |
| 78 | 3-furyl | |
| 79 | 2-(5-NO2-furyl) | |
| 80 | 2-thienyl | |
| 81 | 2-(5-Cl-thienyl) | |
| 82 | 2-(3-Cl-thienyl) | |
| 83 | 3-(thienyl) | |
| 84 | 2-benzofuranyl | |
| 85 | 2-benzothienyl | |
| 86 | 5-isoxazolyl | |
| 87 | 3-(2-Cl-pyridyl) | |
| 88 | 3-(6-Cl-pyridyl) | |
| 89 | 4-(2,6-Cl2-pyridyl) | |
| 90 | 3-(5,6-Cl2-pyridyl) | |
| 91 | 3-(2-phenoxypyridyl) | |

TABLE 10

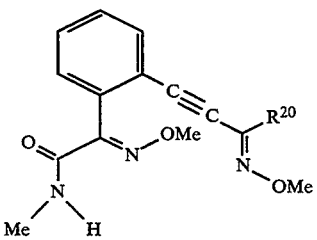

| No. | R20 | phys. data m.p. [°C.] IR [cm−1] 1H-NMR [δ scale] |
|---|---|---|
| 1 | methyl | |
| 2 | ethyl | |
| 3 | n-propyl | |
| 4 | i-propyl | |
| 5 | n-butyl | |
| 6 | i-butyl | |
| 7 | s-butyl | |
| 8 | tert.-butyl | |
| 9 | benzyl | |
| 10 | phenyl | 2.85 (d, 3H); 3.94; 4.10 (CH3); 6.79 (NH), 7.28–7.84 ppm (9H) |
| 11 | 2-Me-phenyl | |
| 12 | 3-Me-phenyl | |
| 13 | 4-Me-phenyl | |
| 14 | 2-F-phenyl | |
| 15 | 3-F-phenyl | |
| 16 | 4-F-phenyl | |
| 17 | 2-Cl-phenyl | |
| 18 | 3-Cl-phenyl | |
| 19 | 4-Cl-phenyl | |
| 20 | 2-Br-phenyl | |
| 21 | 3-Br-phenyl | |
| 22 | 4-Br-phenyl | |

TABLE 10-continued

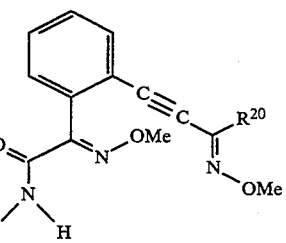

| No. | R20 | phys. data m.p. [°C.] IR [cm−1] 1H-NMR [δ scale] |
|---|---|---|
| 23 | 2-I-phenyl | |
| 24 | 3-I-phenyl | |
| 25 | 4-I-phenyl | |
| 26 | 2-CF3-phenyl | |
| 27 | 3-CF3-phenyl | |
| 28 | 4-CF3-phenyl | |
| 29 | 2-OCH3-phenyl | |
| 30 | 3-OCH3-phenyl | |
| 31 | 4-OCH3-phenyl | |
| 32 | 2-CN-phenyl | |
| 33 | 3-CN-phenyl | |
| 34 | 4-CN-phenyl | |
| 35 | 2-NO2-phenyl | |
| 36 | 3-NO2-phenyl | |
| 37 | 4-NO2-phenyl | |
| 38 | 2-OCF3-phenyl | |
| 39 | 3-OCF3-phenyl | |
| 40 | 4-OCF3-phenyl | |
| 41 | 2-CCl3-phenyl | |
| 42 | 3-CCl3-phenyl | |
| 43 | 4-CCl3-phenyl | |
| 44 | 2-NMe2-phenyl | |
| 45 | 3-NMe2-phenyl | |
| 46 | 4-NMe2-phenyl | |
| 47 | 2-tert.-butylphenyl | |
| 48 | 3-tert.-butylphenyl | |
| 49 | 4-tert.-butylphenyl | |
| 50 | 2-tert.-butoxyphenyl | |
| 51 | 3-tert.-butoxyphenyl | |
| 52 | 4-tert.-butoxyphenyl | |
| 53 | 2-phenylphenyl | |
| 54 | 3-phenylphenyl | |
| 55 | 4-phenylphenyl | |
| 56 | 2-phenoxyphenyl | |
| 57 | 3-phenoxyphenyl | |
| 58 | 4-phenoxyphenyl | |
| 59 | 1-naphthyl | |
| 60 | 2-naphthyl | |
| 61 | 2,3-Me2-phenyl | |
| 62 | 2,4-Me2-phenyl | |
| 63 | 2,5-Me2-phenyl | |
| 64 | 2,6-Me2-phenyl | |
| 65 | 3,4-Me2-phenyl | |
| 66 | 3,5-Me2-phenyl | |
| 67 | 2,4,6-Me3-phenyl | |
| 68 | 2,3-Cl2-phenyl | |
| 69 | 2,4-Cl2-phenyl | |
| 70 | 2,5-Cl2-phenyl | |
| 71 | 2,6-Cl2-phenyl | |
| 72 | 3,4-Cl2-phenyl | |
| 73 | 3,5-Cl2-phenyl | |
| 74 | 2-pyridyl | |
| 75 | 3-pyridyl | |
| 76 | 4-pyridyl | |
| 77 | 2-furyl | |
| 78 | 3-furyl | |
| 79 | 2-(5-NO2-furyl) | |
| 80 | 2-thienyl | |
| 81 | 2-(5-Cl-thienyl) | |
| 82 | 2-(3-Cl-thienyl) | |
| 83 | 3-(thienyl) | |
| 84 | 2-benzofuranyl | |
| 85 | 2-benzothienyl | |
| 86 | 5-isoxazolyl | |
| 87 | 3-(2-Cl-pyridyl) | |

TABLE 10-continued

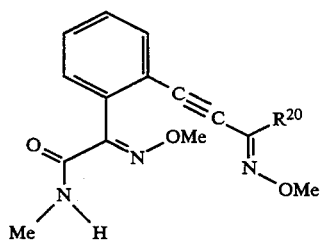

| No. | R[20] | phys. data<br>m.p. [°C.]<br>IR [cm$^{-1}$]<br>$^1$H-NMR [δ scale] |
|---|---|---|
| 88 | 3-(6-Cl-pyridyl) | |
| 89 | 4-(2,6-Cl$_2$-pyridyl) | |
| 90 | 3-(5,6-Cl$_2$-pyridyl) | |
| 91 | 3-(2-phenoxypyridyl) | |

The novel compounds are suitable as fungicides.

The fungicidal compounds according to the invention, or agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

Normally, the plants are sprayed or dusted with the active ingredients or the seeds of the plants are treated with the active ingredients.

The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin-sulfite waste liquors and methylcellulose.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

Examples of such formulations are given below.

I. A solution of 90 parts by weight of compound no. 1 from Table 2 and 10 parts by weight of N-methyl-α-pyrrolidone, which is suitable for application in the form of very fine drops.

II. A mixture of 20 parts by weight of compound no. 24 from Table 2, 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By finely dispersing the mixture in water, a dispersion is obtained.

III. An aqueous dispersion of 20 parts by weight of compound no. 25 from Table 2, 40 parts by weight of cyclohexanone, 30 parts by weight of isobutanol, 20 parts by weight of the adduct of 40 moles of ethylene oxide and 1 mole of castor oil.

IV. An aqueous dispersion of 20 parts by weight of compound no. 26 from Table 2, 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil.

V. A hammer-milled mixture of 80 parts by weight of compound no. 31 from Table 2, 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel. By finely dispersing the mixture in water, a spray liquor is obtained.

VI. An intimate mixture of 3 parts by weight of compound no. 33 from Table 2 and 97 parts by weight of particulate kaolin. The dust contains 3 wt % of the active ingredient.

VII. An intimate mixture of 30 parts by weight of compound no. 34 from Table 2, 92 parts by weight of powdered silica gel and 8 parts by weight of paraffin oil sprayed onto the surface of this silica gel. This formulation of the active ingredient exhibits good adherence.

VIII. A stable aqueous dispersion of 40 parts by weight of compound no. 35 from Table 2, 10 parts of the sodium salt of a phenolsulfonic acid-urea-formaldehyde condensate, 2 parts of silica gel and 48 parts of water, which dispersion can be further diluted.

IX. A stable oily dispersion of 20 parts by weight of compound no. 42 from Table 2, 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil.

The novel compounds are extremely effective on a broad spectrum of phytopathogenic fungi, in particular those from the class consisting of the Ascomycetes and Basidiomycetes. Some of them have a remarkably high systemic mobility and action after application to the soil and particularly to foliage.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The compounds are applied by treating the seeds, plants, materials or soil to be protected against fungus attack with a fungicidally effective amount of the active ingredients.

The compounds may be applied before or after infection of the materials, plants or seeds by the fungi.

The compounds I are particularly useful for controlling the following plant diseases:
Erysiphe graminis in cereals,
Erysiphe cichoracearum and Sphaerotheca fuliginea in cucurbits,
Podosphaera leucotricha in apples,
Uncinula necator in vines,
Puccinia species in cereals,
Rhizoctonia solani in cotton,
Ustilago species in cereals and sugar cane,
Venturia inaequalis (scab) in apples,
H elminthosporium species in cereals,
Septoria nodorum in wheat,
Botrytis cinerea (gray mold) in strawberries and grapes,
Cercospora arachidicola in groundnuts,
Pseudocercosporella herpotrichoides in wheat and barley,
Pyricularia oryzae in rice,
Phytophthora infestans in potatoes and tomatoes,
Fusarium and Verticillium species in various plants,
Plasmopara viticola in grapes,
Alternaria species in fruit and vegetables.

The novel compounds may also be used for protecting materials (timber), for example against Paecilomyces variotii.

The fungicidal agents generally contain from 0.1 to 95, and preferably from 0.5 to 90, wt % of active ingredient.

The application rates depend on the type of effect desired, but are generally from 0.02 to 3 kg of active ingredient per hectare.

When the active ingredients are used for treating seed, application rates of from 0.001 to 50, and preferably from 0.01 to 10, g per kg of seed are generally required.

When the agents according to the invention are used as fungicides, they may be employed together with other active ingredients, e.g., herbicides, insecticides, growth regulators, other fungicides and fertilizers.

When admixed with other fungicides, the spectrum of fungicidal action is in many instances increased.

Use examples

In the active ingredients used for comparison purposes, U, V and W=H, A=CH$_3$ON=, B=CH$_3$O and R=phenyl (compound 1), R=2-chlorophenyl (compound B), and R=4-CF$_3$-phenyl (compound C). All of these compounds are known from EP 253 213.

Use Example 1

Action on cucumber mildew

Young cucumber plants of the "Chinesische Schlange" variety were sprayed to runoff at the two-leaf stage with an aqueous spray liquor. The next day these plants were sprayed with an aqueous conidial suspension of cucumber mildew (Erysiphe cichoracearum and Sphaerotheca fuliginea), and kept in the greenhouse at 20° to 22° C. and a relative humidity of 70 to 80%. The extent of fungus spread was determined 21 days after application of the active ingredients.

The results show that the active ingredients from Table 2, no. 33 (2,33), 2,43; 2,148 and 2,166 have, when applied as a spray liquor containing 63 ppm of active ingredient, a better fungicidal action (10% leaf attack) than prior art comparative active ingredients A, B and C (45% leaf attack).

Use Example 2

Action on Botrytis cinerea in paprika pods (fruit test)

Slices of green paprika pods were sprayed to runoff with aqueous formulations containing 80% of active ingredient and 20% of emulsifier. Two hours after the sprayed-on layer had dried, the slices were inoculated with a spore suspension of Botrytis cinerea containing $1.7 \times 10^6$ spores per ml of a 2% biomalt solution. The inoculated slices were then incubated in moist chambers for 4 days at 18° C. The extent of Botrytis spread on the slices was then assessed visually.

The results show that active ingredients 2,25; 2,35; 2,166 and 2,179, when applied as spray liquors containing 500 ppm of active ingredient, have a better fungicidal action (10% attack) than prior art comparative active ingredient A (30% attack).

Use Example 3

Action on Plasmopara viticola

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 8 days in the greenhouse. Then the leaves were infected with a zoospore suspension of Plasmopara viticola. The plants were first placed for 48 hours in a water vapor-saturated chamber at 24° C. and then in a greenhouse for 5 days at from 20° to 30° C. To accelerate and intensify the sporangiophore discharge, the plants were then again placed in the moist chamber for 16 hours. The extent of fungus attack was then assessed on the undersides of the leaves.

The results show that active ingredients 1,195; 2,25; 2,35; 2,43; 2,86; 2,88; 2,92; 2,94; 2,95 and 2,148, when applied as spray liquors containing 16 ppm of active ingredient, have a better fungicidal action (5% leaf attack) than prior art comparative active ingredient C (35% leaf attack).

We claim:

1. An acetylene derivative of the formula I

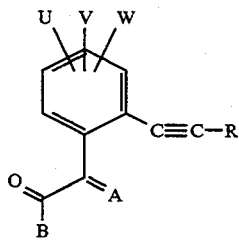

I where

U, V and W are identical or different and are each hydrogen, halogen, nitro, cyano, $C_1$-$C_4$-alkyl or $C_1$-$C_4$-alkoxy, A is $C_1$-$C_4$-alkoximino, B is OH or $C_1$-$C_4$-alkoxy and R is hydrogen, halogen, cyano, $CF_3$, straight-chain or branched $C_1$-$C_{10}$-alkyl, $C_3$-$C_6$-cycloalkyl, unsubstituted or substituted aryl, halo-$C_1$-$C_4$-alkyl, $C_2$-$C_6$-alkenyl, $C_2$-$C_4$-alkynyl, unsubstituted or substituted aryl-$C_1$-$C_4$-alkyl, unsubstituted or substituted aryl-$C_2$-$C_4$-alkenyl, unsubstituted or substituted arylethynyl, $C_1$-$C_4$-alkoxy-$C_1$-$C_4$-alkyl, unsubstituted or substituted aryloxy-$C_1$-$C_4$-alkyl, unsubstituted or substituted arylamino-$C_1$-$C_4$-alkyl, unsubstituted or substituted arylthiomethyl, $C(O)R^1$, $C(O)NR^2R^3$, $C(S)NR^4R^5$, $C(O)SR^6$, $C(S)OR^7$, $C(S)SR^8$, $CH(OH)R^9$, $CH(OR^{10})R^{11}$, $C(OR)R^{18}$ or $C(=N-OR^{19})R^{20}$ and $R^1$–$R^{17}$, $R^{19}$ and $R^{20}$ are identical or different and are each hydrogen, $C_1$-$C_4$-alkyl, unsubstituted or substituted aryl or unsubstituted or substituted arylalkyl, $R^{18}$ is OH, $C_1$-$C_4$-alkoxy or unsubstituted or substituted aryl-$C_1$-$C_4$-alkoxy, the term "unsubstituted or substituted" denoting, in addition to hydrogen, halogen, cyano, nitro, $C_1$-$C_4$-alkyl, $C_1$-$C_4$-alkoxy, $C_1$-$C_4$-haloalkyl, $C_1$-$C_4$-haloalkoxy, $C_1$-$C_4$-alkoximino-$C_1$-$C_4$-alkyl, aryl, aryloxy, benzyl, benzyloxy, $C_3$-$C_6$-cycloalkyl, $C_1$-$C_4$-dialkylamino, $CO_2Me$, $CO_2Et$, formyl or acyl and Me is methyl and Et is ethyl, with the exception of the following individual compounds of the formula I where A=CHOCH$_3$, B=OCH$_3$ and R=phenyl A=CHSCH$_3$, B=OCH$_3$ and R=phenyl A=CHCH$_3$, B=OCH$_3$, and R=phenyl, 2-fluorophenyl, 2-chlorophenyl, 2-bromophenyl, 2-methoxyphenyl, 2-nitrophenyl, 2-methylphenyl, 4-bromophenyl, 4-trifluoromethylphenyl or 4-methylphenyl, A=NOCH$_3$, B=OCH$_3$ and R=phenyl, 2-fluorophenyl, 2-chlorophenyl, 2-bromophenyl, 2-methoxyphenyl, 2-nitrophenyl, 2-methylphenyl, 4-bromophenyl, 4-trifluoromethylphenyl or 4-methylphenyl, A=NOCH$_3$, B=NHCH$_3$, R=CH$_3$, phenyl, A=CHOCH$_3$, B=NHCH$_3$, R=CH$_3$, phenyl and A=CHSCH$_3$, B=NHCH$_3$, R=phenyl.

2. An acetylene derivative of the formula III

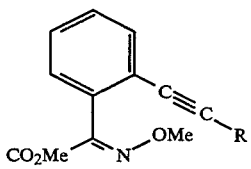

III where R is a defined in claim 1.

3. An acetylene derivative of the formula VII

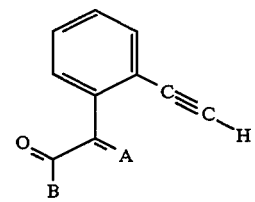

VII where A and B are as defined in claim 1.

4. A fungicide containing an inert carrier and a fungicidally effective amount of an acetylene derivative of the formula I

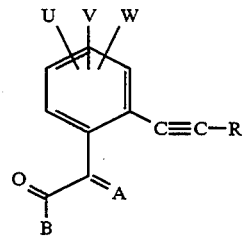

I where

U, V and W are identical or different and are each hydrogen, halogen, nitro, cyano, $C_1$-$C_4$-alkyl or $C_1$-$C_4$-alkoxy, A is $C_1$-$C_4$-alkoximino, B is OH or $C_1$-$C_4$-alkoxy and R is hydrogen, halogen, cyano, $CF_3$, straight-chain or branched $C_1$-$C_{10}$-alkyl, $C_3$-$C_6$-cycloalkyl, unsubstituted or substituted aryl, halo-$C_1$-$C_4$-alkyl, $C_2$-$C_6$-alkenyl, $C_2$-$C_4$-alkynyl, unsubstituted or substituted aryl-$C_1$-$C_4$-alkyl, unsubstituted or substituted aryl-$C_2$-$C_4$-alkenyl, unsubstituted or substituted arylethynyl, $C_1$-$C_4$-alkoxy-$C_1$-$C_4$-alkyl, unsubstituted or substituted aryloxy-$C_1$-$C_4$-alkyl, unsubstituted or substituted arylamino-$C_1$-$C_4$-alkyl, unsubstituted or substituted arylthiomethyl, $C(O)R^1$, $C(O)NR^2R^3$, $C(S)NR^4R^5$, $C(O)SR^6$, $C(S)OR^7$, $C(S)SR^8$, $CH(OH)R^9$, $CH(OR^{10})R^{11}$, $C(OR)R^{18}$ or $C(=N-OR^{19})R^{20}$ and $R^1$–$R^{17}$, $R^{19}$ and $R^{20}$ are identical or different and are each hydrogen, $C_1$-$C_4$-alkyl, unsubstituted or substituted aryl or unsubstituted or substituted arylalkyl, $R^{18}$ is OH, $C_1$-$C_4$-alkoxy or unsubstituted or substituted aryl-$C_1$-$C_4$-alkoxy, the term "unsubstituted or substituted" denoting, in addition to hydrogen, halogen, cyano, nitro, $C_1$-$C_4$-alkyl, $C_1$-$C_4$-alkoxy, $C_1$-$C_4$-haloalkyl, $C_1$-$C_4$-haloalkoxy, $C_1$-$C_4$-alkoximino-$C_1$-$C_4$-alkyl, aryl, aryloxy, benzyl, benzyloxy, $C_3$-$C_6$-cycloalkyl, $C_1$-$C_4$-dialkylamino, $CO_2Me$, $CO_2Et$, formyl or acyl and Me is methyl and Et is ethyl, with the exception of the following individual compounds of the formula I where A=CHOCH$_3$, B=OCH$_3$ and R=phenyl
A=CHSCH$_3$, B=OCH$_3$ and R=phenyl
A=CHCH$_3$, B=OCH$_3$, and R=phenyl, 2-fluorophenyl, 2-chlorophenyl, 2-bromophenyl, 2-methoxyphenyl, 2-nitrophenyl, 2-methylphenyl, 4-bromophenyl, 4-trifluoromethylphenyl or 4-methylphenyl,
A=NOCH$_3$, B=OCH$_3$ and R=phenyl, 2-fluorophenyl, 2-chlorophenyl, 2-bromophenyl, 2-methoxyphenyl, 2-nitrophenyl, 2-methylphenyl, 4-bromophenyl, 4-trifluoromethylphenyl or 4-methylphenyl,
A=NOCH$_3$, B=NHCH$_3$, R=CH$_3$, phenyl,
A=CHOCH$_3$, B=NHCH$_3$, R=CH$_3$, phenyl and
A=CHSCH$_3$, B=NHCH$_3$, R=phenyl.

5. A method of combatting fungi, wherein the fungi, or the materials, plants or seeds to be protected against fungus attack, or the soil are treated with a fungicidally effective amount of a compound of the formula

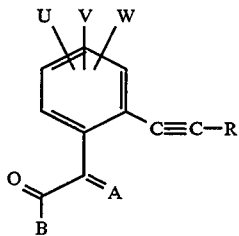

I where
U, V and W are identical or different and are each hydrogen, halogen, nitro, cyano, C$_1$–C$_4$-alkyl or C$_1$–C$_4$-alkoxy,
A is C$_1$–C$_4$-alkoximino,
B is OH or C$_1$–C$_4$-alkoxy and
R is hydrogen, halogen, cyano, CF$_3$, straight-chain or branched C$_1$–C$_{10}$-alkyl, C$_3$–C$_6$-cycloalkyl, unsubstituted or substituted aryl, halo-C$_1$–C$_4$-alkyl, C$_2$–C$_6$-alkenyl, C$_2$–C$_4$-alkynyl, unsubstituted or substituted aryl-C$_1$–C$_4$-alkyl, unsubstituted or substituted aryl-C$_2$–C$_4$-alkenyl, unsubstituted or substituted arylethynyl, C$_1$–C$_4$-alkoxy-C$_1$–C$_4$-alkyl, unsubstituted or substituted aryloxy-C$_1$–C$_4$-alkyl, unsubstituted or substituted arylamino-C$_1$–C$_4$-alkyl, unsubstituted or substituted arylthiomethyl, C(O)R$^1$, C(O)NR$^1$R$^3$, C(S)NR$^4$R$^5$, C(O)SR$^6$, C(S)OR$^7$, C(S)SR$^8$, CH(OH)R$^9$, CH(OR$^{10}$)R$^{11}$, C(OR)R$^{18}$ or C(=N—OR$^{19}$)R$^{20}$ and
R$^1$–R$^{17}$, R$^{19}$ and R$^{20}$ are identical or different and are each hydrogen, C$^1$–C$_4$-alkyl, unsubstituted or substituted aryl or unsubstituted or substituted arylalkyl,
R$^{18}$ is OH, C$_1$–C$_4$-alkoxy or unsubstituted or substituted aryl-C$_1$–C$_4$-alkoxy,
the term "unsubstituted or substituted" denoting, in addition to hydrogen, halogen, cyano, nitro, C$_1$–C$_4$-alkyl, C$_1$–C$_4$-alkoxy, C$_1$–C$_4$-haloalkyl, C$_1$–C$_4$-haloalkoxy, C$_1$–C$_4$-alkoximino-C$_1$–C$_4$-alkyl, aryl, aryloxy, benzyl, benzyloxy, C$_3$–C$_6$-cycloalkyl, C$_1$–C$_4$-dialkylamino, CO$_2$Me, CO$_2$Et, formyl or acyl and Me is methyl and Et is ethyl, with the exception of the following individual compounds of the formula I where A=CHOCH$_3$, B=OCH$_3$ and R=phenyl
A=CHSCH$_3$, B=OCH$_3$ and R=phenyl
A=CHCH$_3$, B=OCH$_3$, and R=phenyl, 2-fluorophenyl, 2-chlorophenyl, 2-bromophenyl, 2-methoxyphenyl, 2-nitrophenyl, 2-methylphenyl, 4-bromophenyl, 4-trifluoromethylphenyl or 4-methylphenyl,
A=NOCH$_3$, B=OCH$_3$ and R=phenyl, 2-fluorophenyl, 2-chlorophenyl, 2-bromophenyl, 2-methoxyphenyl, 2-nitrophenyl, 2-methylphenyl, 4-bromophenyl, 4-trifluoromethylphenyl or 4-methylphenyl,
A=NOCH$_3$, B=NHCH$_3$, R=CH$_3$, phenyl,
A=CHOCH$_3$, B=NHCH$_3$, R=CH$_3$, phenyl and
A=CHSCH$_3$, B=NHCH$_3$, R=phenyl.

6. The acetylene derivative of claim 1, wherein R is hydrogen, halogen, cyano, CF$_3$, straight-chain or branched C$_1$–C$_{10}$-alkyl, C$_3$–C$_6$-cycloalkyl, halo-C$_1$–C$_4$-alkyl, C$_2$–C$_6$-alkenyl, C$_2$–C$_4$-alkynyl, unsubstituted or substituted aryl-C$_1$–C$_4$-alkyl, unsubstituted or substituted aryl-C$_2$–C$_4$-alkenyl, unsubstituted or substituted aryl-ethynyl, C$_1$–C$_4$-alkoxy-C$_1$–C$_4$-alkyl, unsubstituted or substituted aryloxy-C$_1$–C$_4$-alkyl, unsubstituted or substituted arylamino-C$_1$–C$_4$-alkyl, unsubstituted or substituted arylthiomethyl C(O)R$^1$, C(O)NR$^2$R$^3$, C(S)NR$^4$R$^5$, C(O)SR$^6$, C(S)OR$^7$, C(S)SR$^8$, CH(OH)R$^9$, CH(OR$^{10}$)R$^{11}$, C(O)R$^{16}$ or C(=N—OR$^{19}$)R$^{20}$.

7. The acetylene derivative of claim 2, wherein R is phenyl substituted with halogen, cyano, nitro, C$_1$–C$_4$ alkoxy, C$_1$–C$_4$-haloalkyl, C$_1$–C$_4$-haloalkoxy, C$_1$–C$_4$-alkoxyimino-C$_1$–C$_4$-alkyl, aryl, aryloxy, benzyl, benzyloxy, C$_3$–C$_6$-cycloalkyl, C$_1$–C$_4$-dialkylamino, CO$_2$Me, CO$_2$Et, formyl or acyl.

8. The acetylene derivative of claim 7, wherein R is selected from the group consisting of 2,3-Me$_2$-phenyl, 2,4-Me$_2$-phenyl, 2,5-Me$_2$-phenyl, 2,6-Me$_2$-phenyl, 3,4-Me$_2$-phenyl, 3,5-Me$_2$-phenyl and 2,4,6-Me$_3$-phenyl.

9. The acetylene derivative of claim 2, wherein R is selected from the group consisting of 2-CN-phenyl, 3-CN-phenyl, 4-CN-phenyl, 2-(CH$_2$CN)-phenyl, 3-(CH$_2$CN)-phenyl and 4-(CH$_2$CN)-phenyl.

10. The acetylene derivative of claim 9, wherein R is 3-(CH$_2$CN)-phenyl.

* * * * *